US012390097B2

(12) United States Patent
Iwane

(10) Patent No.: US 12,390,097 B2
(45) Date of Patent: Aug. 19, 2025

(54) ENDOSCOPE SYSTEM AND METHOD OF OPERATING ENDOSCOPE SYSTEM

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 338 days.

(21) Appl. No.: 17/931,525

(22) Filed: Sep. 12, 2022

(65) Prior Publication Data
US 2023/0000308 A1 Jan. 5, 2023

Related U.S. Application Data

(63) Continuation of application No. PCT/JP2021/005938, filed on Feb. 17, 2021.

(30) Foreign Application Priority Data

Mar. 13, 2020 (JP) .................................. 2020-044552

(51) Int. Cl.
*A61B 1/06* (2006.01)
*A61B 1/00* (2006.01)
(52) U.S. Cl.
CPC ........ *A61B 1/0655* (2022.02); *A61B 1/00006* (2013.01); *A61B 1/000095* (2022.02); *A61B 1/0002* (2013.01); *A61B 1/0005* (2013.01); *A61B 1/0638* (2013.01); *A61B 1/0669* (2013.01); *A61B 1/0684* (2013.01)
(58) Field of Classification Search
None
See application file for complete search history.

(56) References Cited

U.S. PATENT DOCUMENTS

| 5,896,166 A * | 4/1999 | D'Alfonso ............. H04N 23/66 348/E5.043 |
| 8,723,965 B2 | 5/2014 | Ishii et al. |
| 11,759,092 B2 | 9/2023 | Oosake et al. |

(Continued)

FOREIGN PATENT DOCUMENTS

| CN | 110381807 A | 10/2019 |
| JP | H03-016470 A | 1/1991 |

(Continued)

OTHER PUBLICATIONS

International Search Report issued in PCT/JP2021/005938; mailed May 11, 2021.
Written Opinion of the International Searching Authority issued in PCT/JP2021/005938; mailed May 11, 2021.
An Office Action; mailed by the China State Intellectual Property Office of the People's Republic of China on Sep. 20, 2024, which corresponds to Chinese Patent Application No. 202180020927.X and is related to U.S. Appl. No. 17/931,525.

(Continued)

*Primary Examiner* — Anh Tuan T Nguyen
*Assistant Examiner* — Jae Woo
(74) *Attorney, Agent, or Firm* — Studebaker Brackett PLLC

(57) ABSTRACT

An image processor selects, when a processing start operation for starting image storage processing is performed, a first image and a second image that satisfy a preset selection condition from a plurality of the first images and a plurality of the second images acquired in a target period including a time when the processing start operation is performed, for the image storage processing. A light source processor performs control to switch, out of a first illumination light beam and a second illumination light beam, one being emitted to the other to emit the other, during a target period.

16 Claims, 22 Drawing Sheets

(56) References Cited

U.S. PATENT DOCUMENTS

| | | | | |
|---|---|---|---|---|
| 2013/0058573 A1* | 3/2013 | Suzuki | ............ | A61B 1/045 |
| | | | | 382/167 |
| 2013/0245411 A1* | 9/2013 | Saito | ............ | A61B 1/000094 |
| | | | | 600/339 |
| 2013/0271587 A1* | 10/2013 | Tsuyuki | ............ | A61B 1/051 |
| | | | | 348/71 |
| 2014/0066784 A1* | 3/2014 | Yokota | ............ | A61B 1/0655 |
| | | | | 600/476 |
| 2014/0171737 A1* | 6/2014 | Kagaya | ............ | H04N 25/531 |
| | | | | 600/109 |
| 2015/0272429 A1* | 10/2015 | Shigeta | ............ | A61B 1/0002 |
| | | | | 348/65 |
| 2020/0015656 A1* | 1/2020 | Tsuyuki | ............ | A61B 1/051 |
| 2020/0138275 A1* | 5/2020 | Homma | ............ | G06T 7/0012 |
| 2020/0260933 A1 | 8/2020 | Kubo | | |
| 2020/0305700 A1* | 10/2020 | Kamon | ............ | A61B 1/045 |

FOREIGN PATENT DOCUMENTS

| | | |
|---|---|---|
| JP | 2013-188364 A | 9/2013 |
| JP | 5499050 B2 | 5/2014 |
| JP | 2015-47402 A | 3/2015 |
| WO | 2019/093256 A1 | 5/2019 |
| WO | 2019/130964 A1 | 7/2019 |

OTHER PUBLICATIONS

The extended European search report issued by the European Patent Office on Aug. 4, 2023, which corresponds to European Patent Application No. 21767891.1.

An Office Action; "Notice of Reasons for Refusal," mailed by the Japanese Patent Office on Oct. 17, 2023, which corresponds to Japanese Patent Application No. 2022-505874 and is related to U.S. Appl. No. 17/931,525; with English language translation.

An Office Action; "Decision of Refusal," mailed by the Japanese Patent Office on Jan. 30, 2024, which corresponds to Japanese Patent Application No. 2022-505874 and is related to U.S. Appl. No. 17/931,525; with English language translation.

An Office Action; mailed by the China National Intellectual Property Administration of the People's Republic of China on Jan. 9, 2025, which corresponds to Chinese Patent Application No. 202180020927.X and is related to U.S. Appl. No. 17/931,525.

"Trial and Appeal Decision" mailed by the Japanese Patent Office on Jul. 1, 2025, which corresponds to Japanese Patent Application No. 2022-505874 and is related to U.S. Appl. No. 17/931,525; with English language translation.

* cited by examiner

FIG. 24

| IMAGE (AMOUNT OF BLUR) | a2 (3) | | a3 (2) | | a4 (4) | |
|---|---|---|---|---|---|---|
| | AMOUNT OF BLUR, AMOUNT OF MOVEMENT | TOTAL | AMOUNT OF BLUR, AMOUNT OF MOVEMENT | TOTAL | AMOUNT OF BLUR, AMOUNT OF MOVEMENT | TOTAL |
| b0 (2) | 5, 3 | 8 | 4, 6 | 10 | 6, 7 | 13 |
| b1 (3) | 6, 4 | 10 | 5, 7 | 12 | 7, 8 | 15 |
| b2 (1) | 4, 2 | 6 | 3, 6 | 9 | 5, 7 | 12 |

71

ENDOSCOPE SYSTEM AND METHOD OF OPERATING ENDOSCOPE SYSTEM

CROSS-REFERENCE TO RELATED APPLICATIONS

This application is a Continuation of PCT International Application No. PCT/JP2021/005938 filed on 17 Feb. 2021, which claims priority under 35 U.S.C § 119(a) to Japanese Patent Application No. 2020-044552 filed on 13 Mar. 2020. The above application is hereby expressly incorporated by reference, in its entirety, into the present application.

BACKGROUND OF THE INVENTION

1. Field of the Invention

The present invention relates to an endoscope system that stores a plurality of types of still images through an instruction, and a method of operating the endoscope system.

2. Description of the Related Art

In the medical field, a diagnosis using an endoscope system, which comprises a light source device, an endoscope, and a processor device, has been widely performed. In the diagnosis using the endoscope system, various types of information regarding a surface structure of an observation target, a mucous membrane surface layer, or the like may be obtained by using an image (hereinafter, referred to as an endoscopic image) obtained by imaging the observation target with the endoscope through image-enhanced observation (IEE, image enhanced endoscopy) in which an illumination light beam or the like is devised.

In the diagnosis using IEE, an appropriate diagnosis may be made by acquiring a plurality of types of endoscopic images obtained by a plurality of types of illumination light beams and the like, and comparing in detail or superimposing these endoscopic images. As an endoscope system that uses a plurality of types of images including a normal image obtained through white light observation, an image obtained through IEE, and the like, an endoscope system in which an oxygen saturation observation moving image, a normal observation moving image, and a blood vessel-enhanced observation moving image are juxtaposed and displayed on a display device, and an exposure condition is set and then each observation moving image is stored as a still image in a case where a freeze button is operated while the moving images are displayed, and the like are disclosed (JP2013-188364A, corresponding to US2013/0245411A1).

SUMMARY OF THE INVENTION

In the related art, a plurality of types of still images having less blur is selected and stored, for example, at a point in time back to the past by a certain period from a point in time when an instruction to store the still image is given by the operation of the freeze button while the moving image is displayed. In a plurality of types of illumination light beams, for example, two types of images are compared: an image using the illumination light beam that is used to enhance superficial blood vessels or the like of the observation target and an image using the illumination light beam that is used to enhance medium-depth blood vessels or the like of the same observation target so that information on the depth direction of the observation target can be obtained, which is effective, for example, in a case where a diagnosis on the extent of a lesion is performed.

In order to store a plurality of types of still images corresponding to a plurality of types of illumination light beams, for example, as in the related art, the illumination light beams are switched and the still image is stored for each illumination light beam, whereby various still images are stored. In a case where an observation target is observed and an image thereof is picked up while the plurality of illumination light beams is repeatedly switched, it is preferable that the switching cycle between the illumination light beams used for observation is as long as possible because of problems, such as photosensitivity. However, in this case, it is necessary to select an image of an illumination light beam that is not used for observation when a still image recording instruction is given, and the longer the switching cycle between the illumination light beams is, the larger the difference in time between the plurality of types of stored images is. Since the larger the difference in time between the plurality of types of stored images is, the higher the probability that the positional deviation between the images may occur significantly is due to the motion of the observation target and the like, there is a concern that still images unsuitable for comparison or superimposition may be stored.

On the other hand, in order to reduce the difference in time between the plurality of types of stored images, it is conceivable to reduce the switching cycle between the plurality of illumination light beams to shorten the illumination time of each illumination light beam. However, there is a concern that this method may cause problems, such as light flicker or photosensitivity, which is a trade-off with the difference in time between images.

Further, in JP2013-188364A, in addition to the above, a plurality of illumination light beams is automatically switched in a predetermined order, and moving images corresponding to the respective illumination light beams are simultaneously displayed on a monitor. In this case, a frame rate in a case of one type of illumination light beam is equal to or less than half that of a case where illumination light beams are not switched, and it may be difficult to diagnose, for example, the observation target that may move, through comparison or superimposition between the plurality of types of images.

An object of the present invention is to provide an endoscope system that stores a plurality of types of still images in a state suitable for comparison or superimposition, through a single instruction, and a method of operating the endoscope system.

According to the present invention, there is provided an endoscope system comprising: a plurality of semiconductor light sources that emits light beams having wavelength bands different from each other; a light source processor that performs control to emit each of a plurality of types of illumination light beams of which combinations of light intensity ratios between the plurality of semiconductor light sources are different from each other; and an image processor. The image processor acquires a first image and a second image obtained by imaging an observation target illuminated with a first illumination light beam and a second illumination light beam included in the plurality of types of illumination light beams, respectively, for each frame, performs image storage processing of storing a first image selected from a plurality of the acquired first images and a second image selected from a plurality of the acquired second images, and selects, when a processing start operation for starting the image storage processing is performed, a first image and a second image that satisfy a preset selection condition from the plurality of first images and the plurality of second images acquired in a target period including a time when the processing start operation is performed, for the image storage processing. The light source processor switches, out of the first illumination light beam and the second illumination light beam, one being emitted to the other to emit the other in the target period.

It is preferable that the target period is a period in which the image processor acquires a plurality of the first images which is a preset number and a plurality of the second images which is a preset number.

It is preferable that the target period is a period in which the image processor acquires the first image and the second image that satisfy the selection condition.

It is preferable that the light source processor alternately switches and emits the first illumination light beam and the second illumination light beam at a preset cycle.

It is preferable that the light source processor switches, out of the first illumination light beam and the second illumination light beam, one which is emitted before the processing start operation to the other to emit the other, through the processing start operation, in a case where the processing start operation is performed after a preset period starting from a time when light emission is switched between the first illumination light beam and the second illumination light beam. It is preferable that the light source processor switches, out of the first illumination light beam and the second illumination light beam, one which is emitted after the processing start operation to the other to emit the other, when the target period is passed. It is preferable that the light source processor switches, out of the first illumination light beam and the second illumination light beam, one which is emitted after the processing start operation to the other to emit the other, when a preset period starting from the time of the processing start operation is passed.

It is preferable that the light source processor emits, out of the first illumination light beam and the second illumination light beam, one which is emitted before the processing start operation even after the processing start operation, in a case where the processing start operation is performed in a preset period starting from a time when light emission is switched between the first illumination light beam and the second illumination light beam. It is preferable that the light source processor switches, out of the first illumination light beam and the second illumination light beam, one which is emitted at the time of the processing start operation to the other to emit the other, when the preset period starting from the time when the light emission is switched between the first illumination light beam and the second illumination light beam is passed. It is preferable that the light source processor switches, out of the first illumination light beam and the second illumination light beam, one which is emitted at the time of the processing start operation to the other to emit the other, when a preset period starting from the time of the processing start operation is passed.

It is preferable that the image processor sets the selection condition that a first image having least blur out of the plurality of acquired first images or a second image having least blur out of the plurality of acquired second images is selected.

It is preferable that the image processor sets the selection condition that a first image and a second image having smallest positional deviation between the first image selected from the plurality of acquired first images and the second image selected from the plurality of acquired second images are selected.

It is preferable that the image processor sets the selection condition that a first image and a second image having a smallest difference in brightness between the first image selected from the plurality of acquired first images and the second image selected from the plurality of acquired second images are selected.

It is preferable that the image processor sets the selection condition that a first image and a second image having a smallest difference in acquisition time between the first image selected from the plurality of acquired first images and the second image selected from the plurality of acquired second images are selected.

It is preferable that a display that displays the first image and/or the second image is further provided and the image processor displays the stored first image and/or the stored second image on the display in the target period.

According to the present invention, there is provided a method of operating an endoscope system including a plurality of semiconductor light sources that emits light beams having wavelength bands different from each other, a light source processor that performs control to emit each of a plurality of types of illumination light beams of which combinations of light intensity ratios between the plurality of semiconductor light sources are different from each other, and an image processor. The method comprises: acquiring, by the image processor, a first image and a second image obtained by imaging an observation target illuminated with a first illumination light beam and a second illumination light beam included in the plurality of types of illumination light beams, respectively, for each frame; performing, by the image processor, image storage processing of storing a first image selected from a plurality of the acquired first images and a second image selected from a plurality of the acquired second images; and selecting, by the image processor, when a processing start operation for starting the image storage processing is performed, a first image and a second image that satisfy a preset selection condition from the plurality of first images and the plurality of second images acquired in a target period including a time when the processing start operation is performed, for the image storage processing; and switching, by the light source processor, out of the first illumination light beam and the second illumination light beam, one being emitted to the other to emit the other in the target period.

According to the present invention, it is possible to store a plurality of types of still images in a state suitable for comparison or superimposition, through a single instruction.

BRIEF DESCRIPTION OF THE DRAWINGS

FIG. 24 is a table illustrating the selection condition and the stored endoscopic image.

DESCRIPTION OF THE PREFERRED EMBODIMENTS

Figure 1:
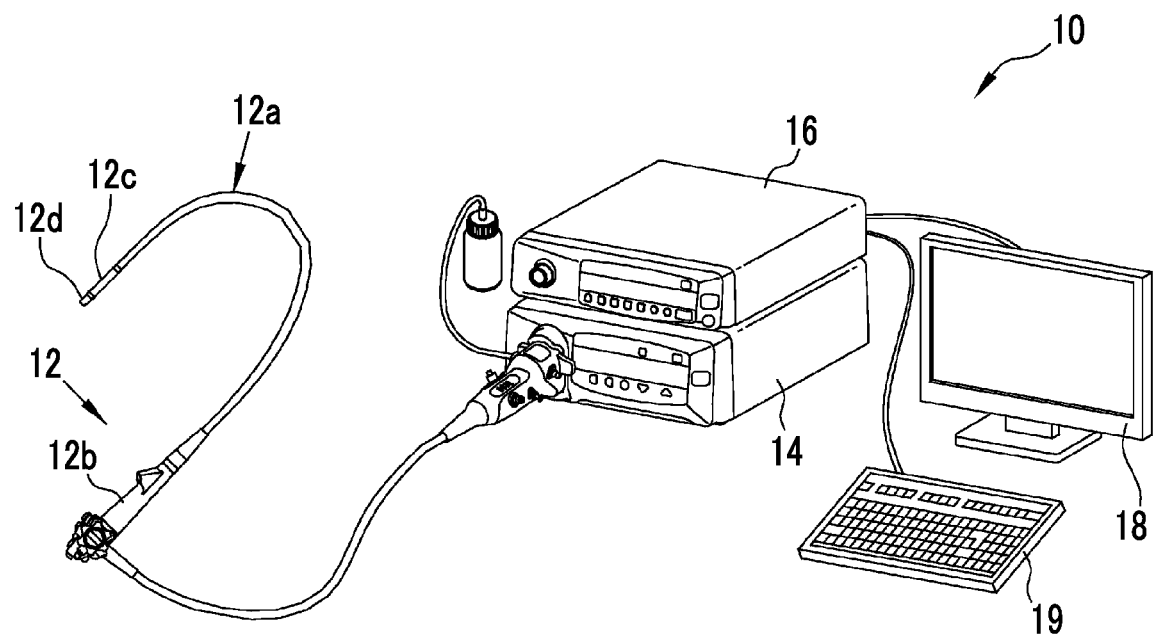
FIG. 1 is an external view of an endoscope system.

In FIG. 1, an endoscope system 10 includes an endoscope 12, a light source device 14, a processor device 16, a display 18, and a keyboard 19. The endoscope 12 is optically connected to the light source device 14 and is electrically connected to the processor device 16. The endoscope 12 includes an insertion part 12a inserted into a body of a subject to be examined having an observation target, an operation part 12b provided at the proximal end portion of the insertion part 12a, and a bendable portion 12c and a distal end portion 12d that are provided in the insertion part 12a on the distal end side. The bendable portion 12c is bent by the operation of an angle knob 12e (see FIG. 2) of the operation part 12b. The bendable portion 12c is bent so that the distal end portion 12d faces a desired direction.

Figure 2:
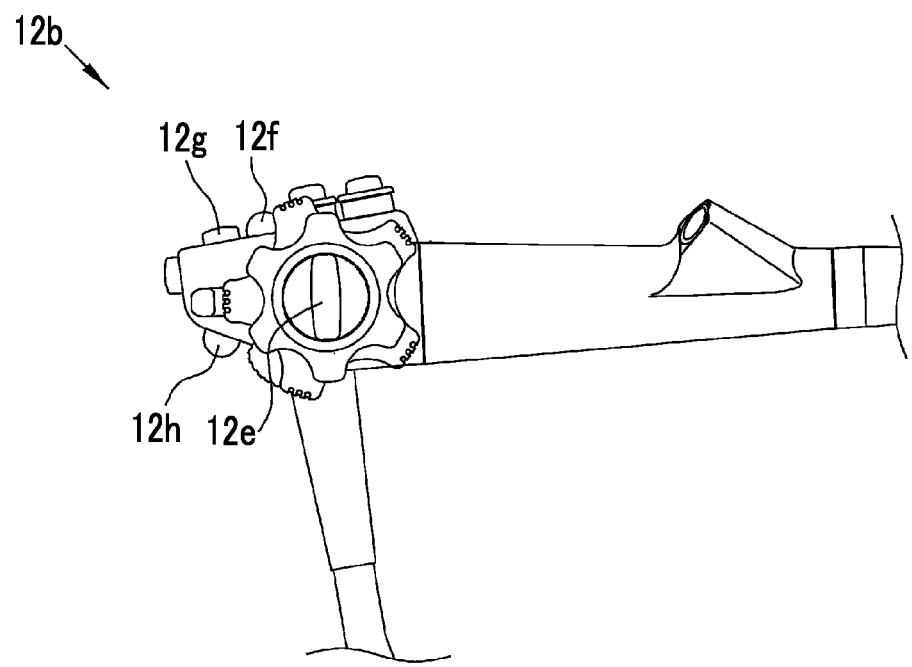
FIG. 2 is an external view of an operation part of an endoscope.

As shown in FIG. 2, the operation part 12b includes a mode changeover switch 12g used for an observation mode switching operation, a zoom operation portion 12h that is used to change an image pickup magnification, and a still image recording instruction portion 12f through which a still image recording instruction is given, in addition to the angle knob 12e. An operation or an instruction using the keyboard 19, a foot switch (not shown), or the like, in addition to the mode changeover switch 12g or a scope switch of the still image recording instruction portion 12f, may be used for the observation mode switching operation, the zoom operation, or the still image recording instruction.

The endoscope system 10 has three modes, that is, a normal observation mode, a special observation mode, and a multi-observation mode. The normal observation mode is a mode for displaying a normal observation image (hereinafter, referred to as a normal image), which is an image with natural color tones obtained by picking up an image of the observation target using white light as an illumination light beam, on the display 18. The special observation mode includes a first special observation mode and a second special observation mode. The first special observation mode is a mode for displaying a first special observation image (hereinafter, referred to as a first image) in which surface layer information such as a superficial blood vessel is enhanced, on the display 18, and the second special observation mode is a mode for displaying a second special observation image (hereinafter, referred to as a second image) in which deep layer information such as a deep blood vessel is enhanced, on the display 18. The multi-observation mode is a mode for automatically switching between the first special observation mode and the second special observation mode.

The processor device 16 is electrically connected to the display 18 and the keyboard 19. The display 18 outputs and displays, for example, the normal image, the first image, the second image, and/or accessory information on these images. The keyboard 19 functions as a user interface that receives an input operation, such as function settings. An external recording unit (not shown) that records images, image information, or the like may be connected to the processor device 16.

Figure 3:
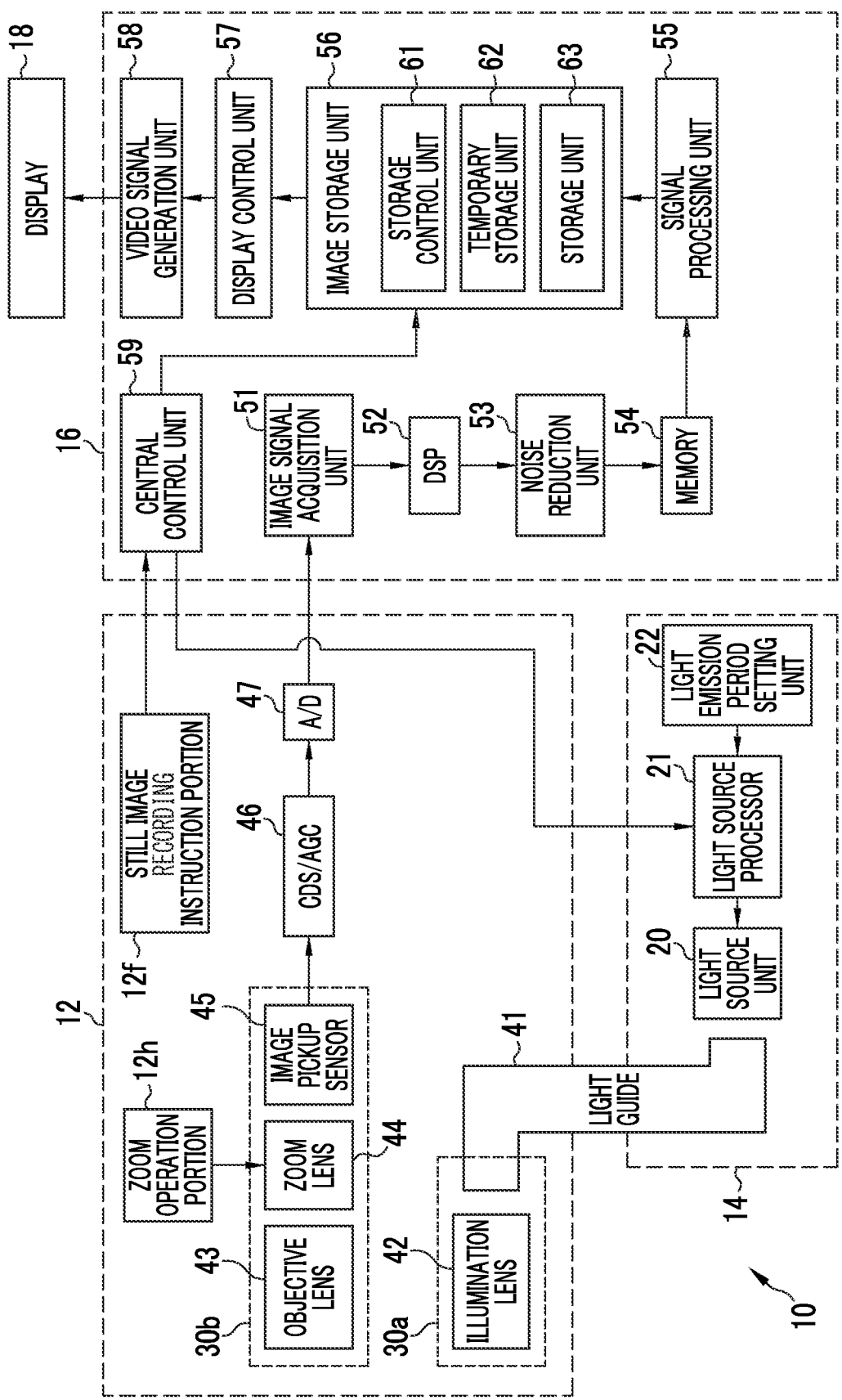
FIG. 3 is a block diagram showing a function of the endoscope system.

In FIG. 3, the light source device 14 emits illumination light beams with which the observation target is irradiated, and comprises a light source unit 20 and a light source processor 21 that controls the light source unit 20. The light source unit 20 is composed of, for example, a semiconductor light source, such as a multi-color light emitting diode (LED), a combination of a laser diode and a phosphor, or a xenon lamp or halogen light source. In addition, the light source unit 20 includes, for example, an optical filter that is used to adjust the wavelength band of a light beam emitted by the LED or the like. The light source processor 21 turns on/off each LED or the like or adjusts the drive current and drive voltage of each LED or the like, thereby controlling the amount of the illumination light beam. Further, the light source processor 21 controls the wavelength band of the illumination light beam by changing the optical filter or the like.

Figure 4:
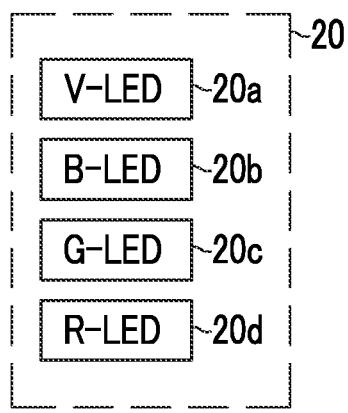
FIG. 4 is a diagram illustrating four-color LEDs provided in a light source unit.

As shown in FIG. 4, in the present embodiment, the light source unit 20 has four-color LEDs, that is, a violet light emitting diode (V-LED) 20a, a blue light emitting diode (B-LED) 20*b*, a green light emitting diode (G-LED) 20*c*, and a red light emitting diode (R-LED) 20*d*.

Figure 5:
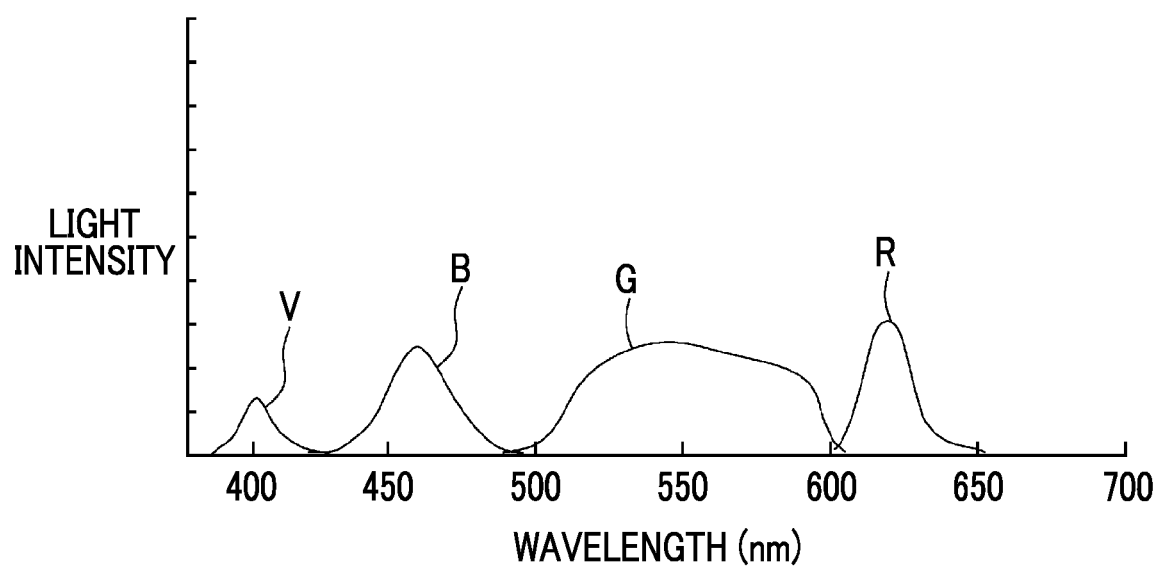
FIG. 5 is a graph showing spectra of violet light V, blue light B, green light G, and red light R.

As shown in FIG. 5, the V-LED 20*a* generates violet light V having a central wavelength of 410±10 nm and a wavelength range of 380 to 420 nm. The B-LED 20*b* generates blue light B having a central wavelength of 450±10 nm and a wavelength range of 420 to 500 nm. The G-LED 20*c* generates green light G having a wavelength range of 480 to 600 nm. The R-LED 20*d* generates red light R having a central wavelength of 620 to 630 nm and a wavelength range of 600 to 650 nm.

The light source processor 21 controls the V-LED 20*a*, the B-LED 20*b*, the G-LED 20*c*, and the R-LED 20*d*. The light source processor 21 controls the respective LEDs 20*a* to 20*d* such that a normal light beam of which the combination of light intensity ratios between violet light V, blue light B, green light G, and red light R is Vc:Bc:Gc:Rc is emitted in the normal observation mode.

Figure 6:
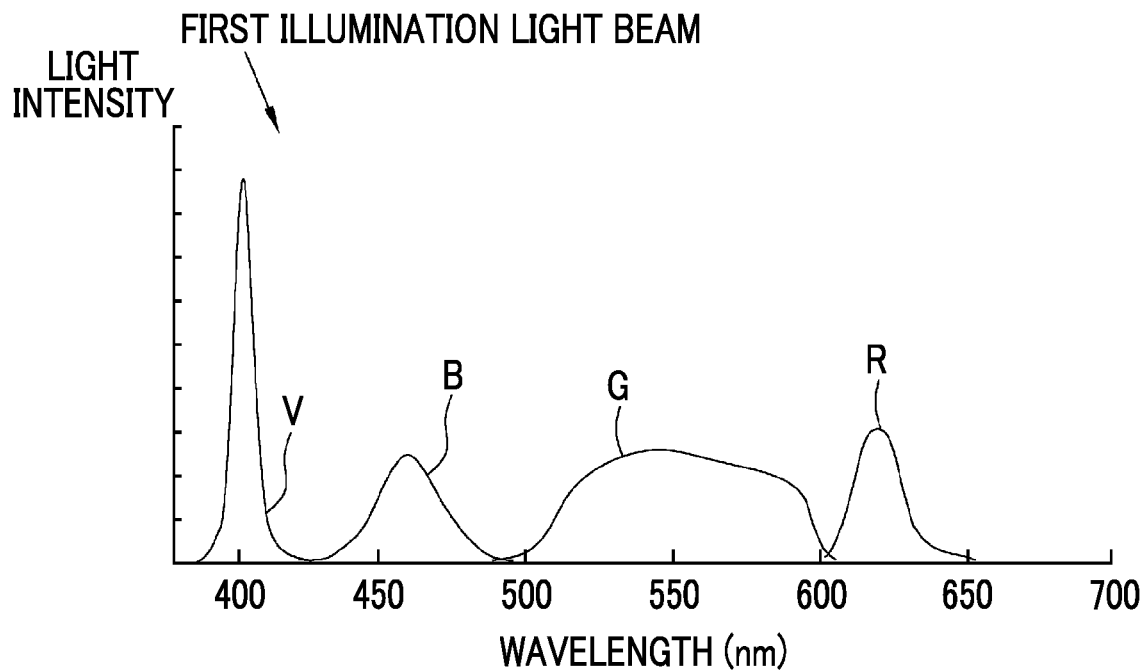
FIG. 6 is a graph showing a spectrum of a first illumination light beam.

The light source processor 21 controls the respective LEDs 20*a* to 20*d* such that a first illumination light beam of which the combination of the light intensity ratios between violet light V, blue light B, green light G, and red light R is Vs1:Bs1:Gs1:Rs1 is emitted in a case where the first special observation mode is set. It is preferable that the first illumination light beam enhances superficial blood vessels. For this purpose, it is preferable that the light intensity of violet light V of the first illumination light beam is set to be higher than the light intensity of blue light B. For example, as shown in FIG. 6, a ratio of the light intensity Vs1 of violet light V to the light intensity Bs1 of blue light B is set to "4:1".

In the present specification, the combination of the light intensity ratios includes a case where the ratio of at least one semiconductor light source is zero. Therefore, the combination of the light intensity ratios includes a case where any one or two or more of the semiconductor light sources are not turned on. For example, a case where only one semiconductor light source is turned on and the other three semiconductor light sources are not turned on as in a case where the combination of the light intensity ratios between violet light V, blue light B, green light G, and red light R is 1:0:0:0 is also regarded that the light source unit 20 has light intensity ratios, and is one of the combinations of the light intensity ratios.

Figure 7:
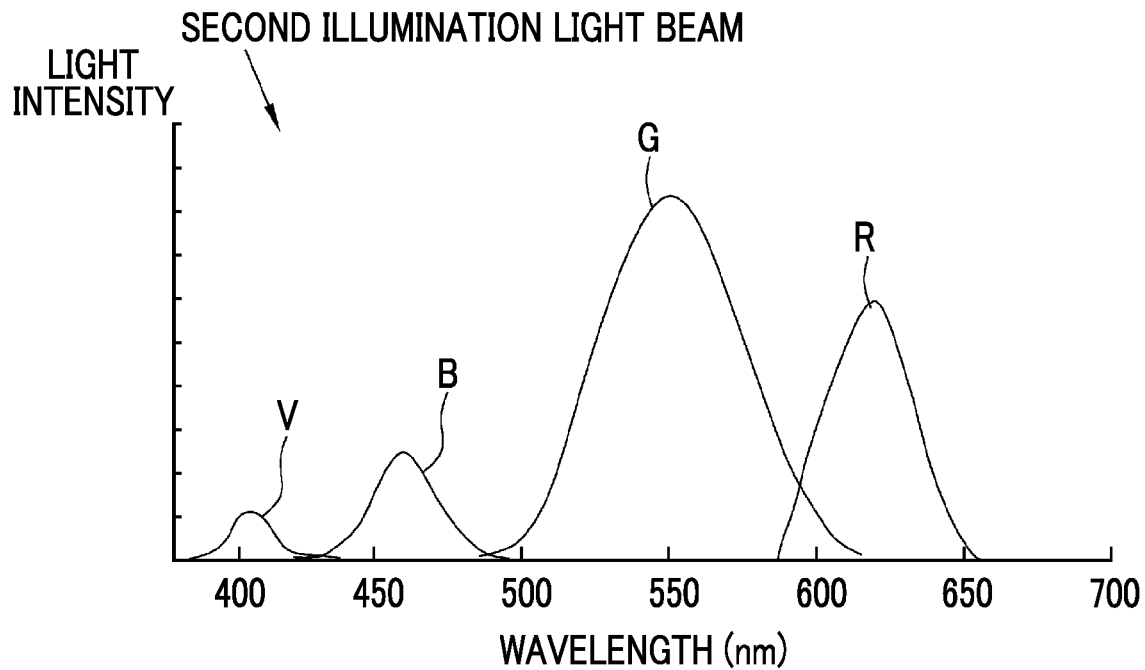
FIG. 7 is a graph showing a spectrum of a second illumination light beam.

The light source processor 21 controls the respective LEDs 20*a* to 20*d* such that a second illumination light beam of which the combination of the light intensity ratios between violet light V, blue light B, green light G, and red light R is Vs2:Bs2:Gs2:Rs2 is emitted in a case where the second special observation mode is set. It is preferable that the second illumination light beam enhances deep blood vessels. For this purpose, it is preferable that the light intensity of blue light B of the second illumination light beam is set to be higher than the light intensity of the violet light V. For example, as shown in FIG. 7, a ratio of the light intensity Vs2 of violet light V to the light intensity Bs2 of blue light B is set to "1:3".

As described above, in the normal observation mode, the first special observation mode, or the second special observation mode, the combinations of the light intensity ratios between violet light V, blue light B, green light G, and red light R, that is, the types of the illumination light beam, are different from each other. It should be noted that an observation mode using a different type of illumination light beam of which a combination of the light intensity ratios is different from the illumination light beams in these observation modes may be used.

The light source processor 21 alternately repeats specific types of illumination light beams, for example, a first period in which the first illumination light beam is continuously emitted and a second period in which the second illumination light beam is continuously emitted, in a case where the multi-observation mode is set. The light emission control performed by the light source processor 21 in the multi-observation mode will be described in detail. The first period in which the first illumination light beam is emitted is followed by the second period in which the second illumination light beam is emitted, and then the first period is repeated, and this cycle is repeated. In the present embodiment, the first period and the second period each correspond to 20 frames.

"Frame" means a unit that is used to control an image pickup sensor 45 (see FIG. 3) that picks up the image of the observation target. For example, "one frame" means a period including at least an exposure period in which the image pickup sensor 45 is exposed to light beams emitted from the observation target and a read-out period in which image signals are read out. In the present embodiment, various types of periods, such as the first period or the second period, are each defined so as to correspond to the "frame" that is a unit of image pickup.

Figure 8:
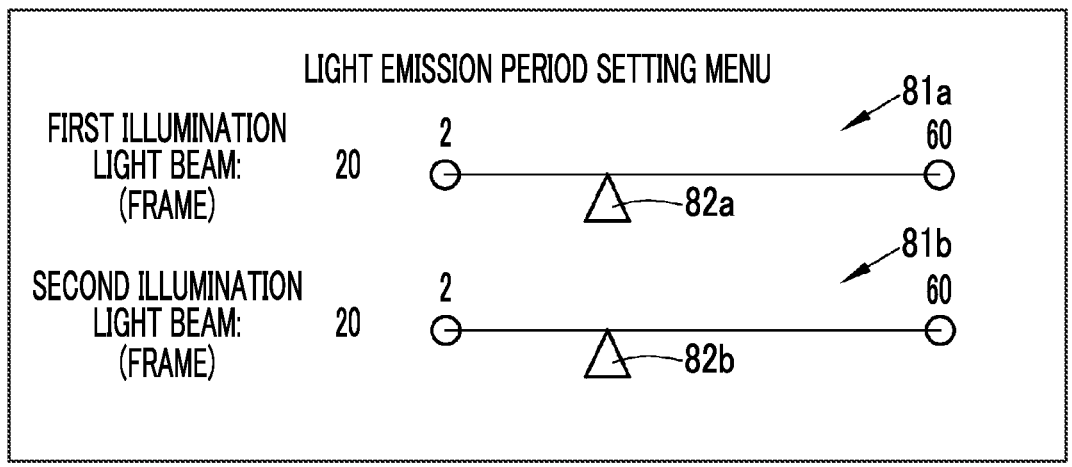
FIG. 8 is a diagram illustrating a light emission period setting menu.

The first period that is the light emission period of the first illumination light beam and the second period that is the light emission period of the second illumination light beam can be appropriately changed by a light emission period setting unit 22 that is connected to the light source processor 21. In a case where an operation for changing the light emission period is received by the operation of the keyboard 19, the light emission period setting unit 22 displays a light emission period setting menu shown in FIG. 8 on the display 18. The first period can be changed, for example, from 2 frames to 60 frames, and the respective light emission periods are assigned onto a slide bar 81*a*. The second period can be also changed, for example, from 2 frames to 60 frames, and the respective light emission periods are assigned onto a slide bar 81*b*.

In a case where the first period is changed, a slider 82*a* is positioned at a position on the slide bar 81*a* indicating a light emission period to be changed by the operation of the keyboard 19, so that the first period is changed. Also in the second period, a slider 82*b* is positioned at a position on the slide bar 81*b* indicating a light emission period to be changed by the operation of the keyboard 19, so that the second period is changed. The slide bar 81*b* is also assigned the light emission periods, for example, from 2 frames to 60 frames. In the present embodiment, in the multi-observation mode, the first period is assigned the light emission period for 20 frames through the slide bar 81*a*, and the second period is assigned the light emission period for 20 frames through the slide bar 81*b*.

Further, the light source processor 21 performs control to switch, out of the first illumination light beam and the second illumination light beam, one being emitted to the other to emit the other in a target period including a time when a processing start operation for starting image storage processing is performed, when the processing start operation is performed. Therefore, illumination light beams are switched once in the target period. For example, in a case where the image storage processing is performed in the first special observation mode, the light source processor 21 switches the first illumination light beam being emitted to the second illumination light beam during the target period. In the second special observation mode, the light source processor 21 switches the second illumination light beam being emitted to the first illumination light beam during the target period. Further, in the multi-observation mode, the light source processor 21 switches the first illumination light beam to the second illumination light beam in a case where the first illumination light beam is being emitted, and switches the second illumination light beam to the first illumination light beam in a case where the second illumination light beam is being emitted. However, in a case where the illumination light beams are periodically switched in the target period as the multi-observation mode, the illumination light beams may not be necessarily further switched. The light source processor 21 is configured as described above, whereby a plurality of types of still images is stored through a single instruction.

A light beam emitted from each of the LEDs 20a to 20d is incident on a light guide 41 through an optical path coupling unit (not shown) that is composed of a mirror, a lens, or the like. The light guide 41 is incorporated in the endoscope 12 and a universal cord (a cord that connects the endoscope 12 to the light source device 14 and the processor device 16). The light guide 41 propagates the light beam from the optical path coupling unit to the distal end portion 12d of the endoscope 12.

The distal end portion 12d of the endoscope 12 is provided with an illumination optical system 30a and an image pickup optical system 30b. The illumination optical system 30a has an illumination lens 42, and the observation target is irradiated with the illumination light beam propagated by the light guide 41, through the illumination lens 42. The image pickup optical system 30b has an objective lens 43, a zoom lens 44, and an image pickup sensor 45. Various types of light beams, such as light reflected from the observation target, scattered light, and fluorescence, are incident on the image pickup sensor 45 through the objective lens 43 and the zoom lens 44. With this, the image of the observation target is formed on the image pickup sensor 45. The zoom lens 44 freely moves between the telephoto end and the wide end with the operation of the zoom operation portion 12h, and magnifies and reduces the observation target of which the image is formed on the image pickup sensor 45.

The image pickup sensor 45 is a color image pickup sensor provided with any one of a red (R) color filter, a green (G) color filter, or a blue (B) color filter for each pixel, and picks up the image of the observation target to output image signals of respective RGB colors. A charge coupled device (CCD) image pickup sensor or a complementary metal-oxide semiconductor (CMOS) image pickup sensor can be used as the image pickup sensor 45. Alternatively, a complementary color image pickup sensor provided with color filters of complementary colors, that is, cyan (C), magenta (M), yellow (Y), and green (G), may be used instead of the image pickup sensor 45 provided with color filters of the primary colors. In a case where the complementary color image pickup sensor is used, the image signals of four colors of CMYG are output. Therefore, the same RGB image signals as those of the image pickup sensor 45 can be obtained by converting the image signals of the four colors of CMYG into the image signals of the three colors of RGB through the complementary color-primary color conversion. Alternatively, a monochrome image pickup sensor that is not provided with color filters may be used instead of the image pickup sensor 45.

The image pickup sensor 45 is driven and controlled by an image pickup control unit (not shown). The image pickup control unit is controlled by a central control unit 59 (see FIG. 3). The control performed by the image pickup control unit differs depending on the respective modes. In the normal observation mode, the image pickup control unit controls the image pickup sensor 45 to pick up the image of the observation target illuminated with the normal light beam. With this, Bc image signals are output from B pixels of the image pickup sensor 45, Gc image signals are output from G pixels thereof, and Rc image signals are output from R pixels thereof. In the special observation mode or the multi-observation mode, the image pickup control unit controls the image pickup sensor 45 to pick up the image of the observation target illuminated with a special light beam. With this, in the first special observation mode, Bs1 image signals are output from the B pixels of the image pickup sensor 45, Gs1 image signals are output from the G pixels thereof, and Rs1 image signals are output from the R pixels thereof. Similarly, in the second special observation mode, Bs2 image signals are output from the B pixels of the image pickup sensor 45, Gs2 image signals are output from the G pixels thereof, and Rs2 image signals are output from the R pixels thereof.

A correlated double sampling/automatic gain control (CDS/AGC) circuit 46 performs correlated double sampling (CDS) or automatic gain control (AGC) on the analog image signals obtained from the image pickup sensor 45. The image signals that have been passed through the CDS/AGC circuit 46 are converted into digital image signals by an analog/digital (A/D) converter 47. The digital image signals that have been subjected to A/D conversion are input to the processor device 16.

In the processor device 16, a program related to processing such as image storage processing is stored in a program memory (not shown). In the processor device 16, the program stored in the program memory operates through the central control unit 59 composed of the image processor, whereby functions of an image signal acquisition unit 51, a digital signal processor (DSP) 52, a noise reduction unit 53, a memory 54, a signal processing unit 55, an image storage unit 56, a display control unit 57, a video signal generation unit 58, and the central control unit 59 are realized. The image storage unit 56 comprises a storage control unit 61, a temporary storage unit 62, and a storage unit 63, and the program stored in the program memory operates through the central control unit 59 composed of the image processor, whereby these functions are also realized as in the above. Further, the central control unit 59 receives information input from the endoscope 12 and the light source device 14, and controls each unit of the processor device 16 and controls the endoscope 12 or the light source device 14, on the basis of the received information. Further, the central control unit 59 also receives information, such as an instruction input from the keyboard 19.

The image signal acquisition unit 51, which is an image acquisition unit, acquires the digital image signals of an endoscopic image, which are input from the endoscope 12. The image signal acquisition unit 51 acquires image signals obtained by imaging the observation target illuminated with each illumination light beam, for each frame. The acquired image signals are transmitted to the DSP 52. The DSP 52 performs digital signal processing, such as color correction processing, on the received image signals. The noise reduction unit 53 performs noise reduction processing, which is performed through, for example, a moving average method or median filtering method, on the image signals that have been subjected to the color correction processing and the like by the DSP 52. The image signals with reduced noise are stored in the memory 54.

The signal processing unit 55 acquires the noise-reduced image signals from the memory 54. Then, signal processing, such as color conversion processing, hue enhancement processing, and structure enhancement processing, is performed as necessary on the acquired image signals, and a color endoscopic image in which the observation target is imaged is generated.

In the normal observation mode, the signal processing unit 55 performs image processing for a normal observation mode, such as color conversion processing, hue enhancement processing, and structure enhancement processing, on the input noise-reduced image signals for one frame. The image signals that have been subjected to the image processing for a normal observation mode are input to the image storage unit 56 as a normal image.

In the special observation mode or the multi-observation mode, the signal processing unit 55 performs image processing for a first special observation mode or for a second special observation mode, such as color conversion processing, hue enhancement processing, and structure enhancement processing, on the noise-reduced image signals for one frame input in the first special observation mode or the second special observation mode. The image signals that have been subjected to the image processing for a first special observation mode or for a second special observation mode are input to the image storage unit 56 as the first image or the second image.

Since the endoscopic image generated by the signal processing unit 55 is a normal observation image in a case where the observation mode is the normal observation mode and the endoscopic image generated by the signal processing unit 55 is a special observation image in a case where the observation mode is the special observation mode, the contents of the color conversion processing, the hue enhancement processing, and the structure enhancement processing differ depending on the observation modes. In the case of the normal observation mode, the signal processing unit 55 generates the normal observation image by performing the above various types of signal processing for making the observation target have natural color tones. In the case of the special observation mode, the signal processing unit 55 generates the special observation image including the first image and the second image by performing the above various types of signal processing for enhancing, for example, the blood vessels of the observation target.

The semiconductor light sources include a first semiconductor light source that emits violet light V (first narrow-band light beam) having a wavelength band of which the central wavelength is 410±10 nm and the wavelength range is 420 to 500 nm, and a second semiconductor light source that emits blue light B (second narrow-band light beam) having a wavelength band of which the central wavelength is 450±10 nm and the wavelength range is 380 to 420 nm. Therefore, in the special observation image generated by the signal processing unit 55, blood vessels (so-called superficial blood vessels) or blood located at a relatively shallow position in the observation target with a surface of the mucous membrane as a reference has magenta-based color (for example, brown color) in the first image, and blood vessels (so-called medium-depth blood vessels) located at a relatively deep position in the observation target with the surface of the mucous membrane as a reference have cyan-based color (for example, green color) in the second image. Therefore, the blood vessels or hemorrhage (blood) of the observation target is enhanced by a difference in color with respect to the mucous membrane represented by pink-based color.

Figure 9:
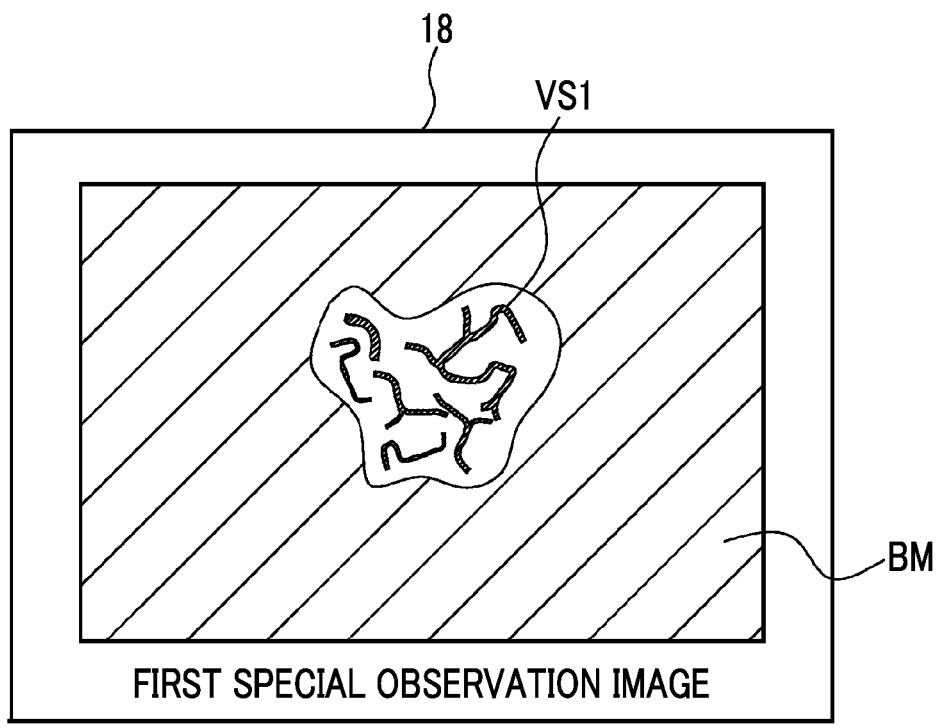
FIG. 9 is an image diagram showing a first special observation image.
Figure 10:
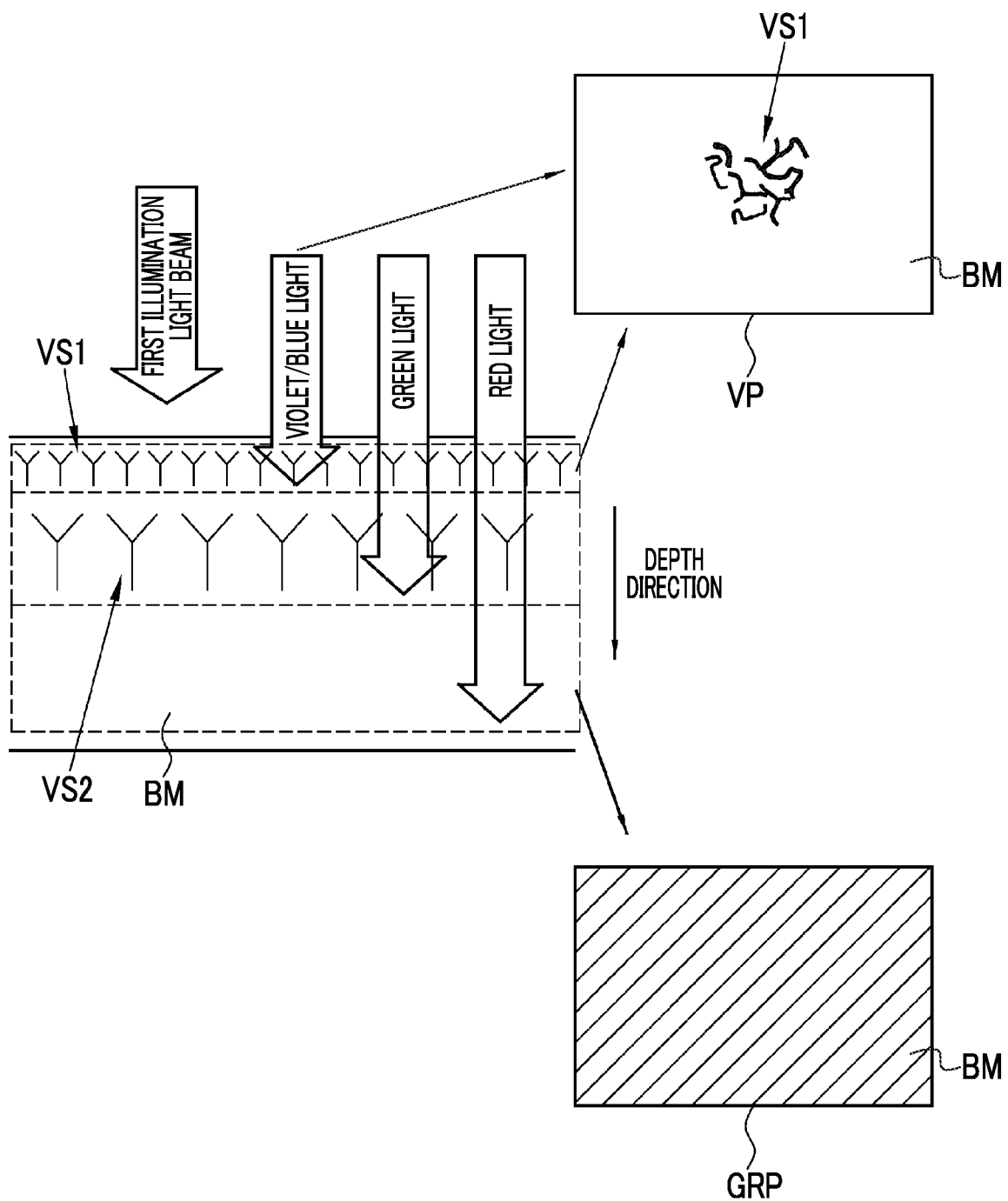
FIG. 10 is a diagram illustrating a violet and blue light image and a green and red light image that are obtained in a case where an observation target is illuminated with the first illumination light beam.

As shown in FIG. 9, an image in which a background mucous membrane BM and superficial blood vessels VS1, out of the observation targets, are shown is displayed in the first image. The first image is obtained on the basis of the first illumination light beam including violet light, blue light, green light, and red light. As shown in FIG. 10, in a case where the observation target is illuminated with the first illumination light beam, violet light V and blue light B of the first illumination light beam reach a surface layer where the superficial blood vessels VS1 are distributed. Accordingly, a violet light image VP obtained on the basis of the reflected light of violet light V and blue light B includes an image of the superficial blood vessels VS1. Here, since the light intensity of violet light V is higher than the light intensity of blue light B, the image obtained on the basis of the reflected light of violet light V and blue light B is referred to as a violet light image VP. Further, green light G and red light R of the first illumination light beam reach the background mucous membrane BM that is distributed at a position deeper than the positions of the superficial blood vessels VS1 and deep blood vessels VS2 (blood vessels located at positions deeper than the positions of the superficial blood vessels VS1). Accordingly, a green and red light image GRP obtained on the basis of the reflected light of green light G and red light R includes an image of the background mucous membrane BM. As described above, since the first image is an image in which the violet light image VP and the green and red light image GRP are combined with each other, the image of the background mucous membrane BM and the superficial blood vessels VS1 is displayed.

Figure 11:
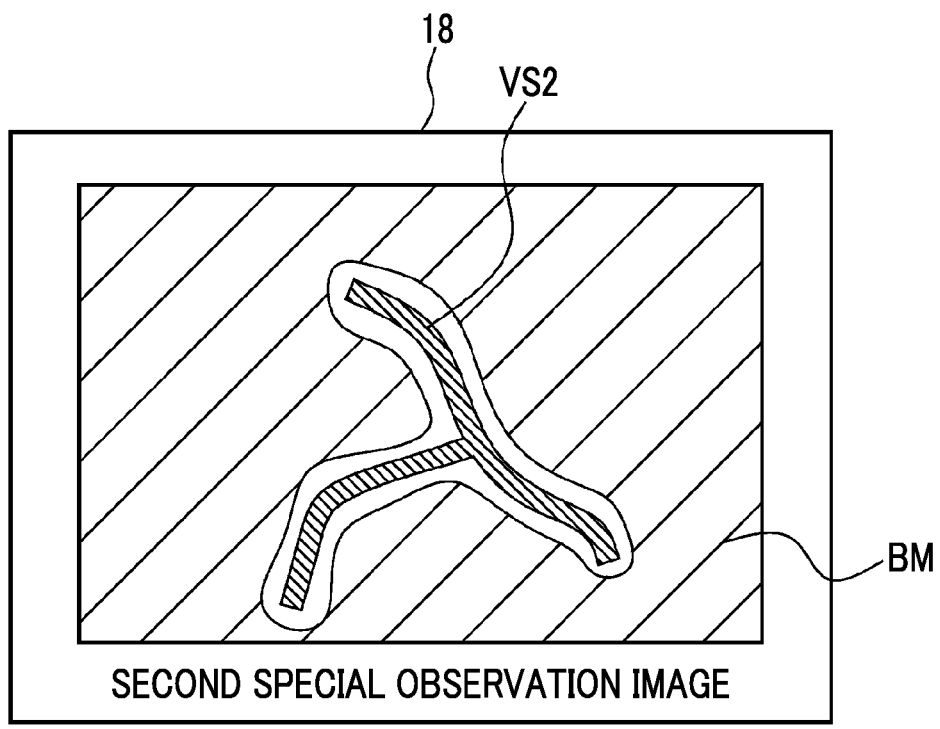
FIG. 11 is an image diagram showing a second special observation image.
Figure 12:
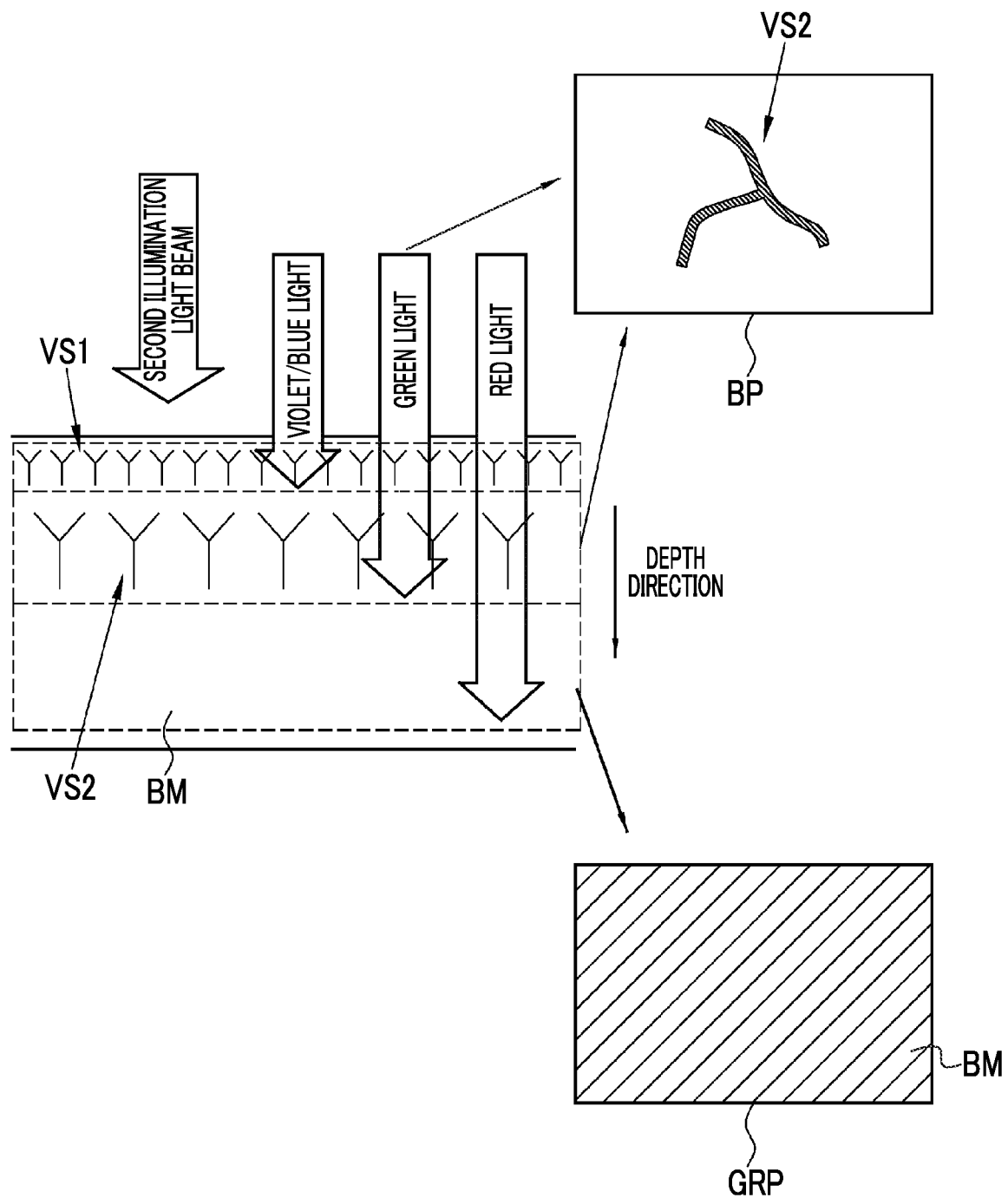
FIG. 12 is a diagram illustrating a violet and blue light image and a green and red light image that are obtained in a case where an observation target is illuminated with the second illumination light beam.

As shown in FIG. 11, an image in which the background mucous membrane BM and deep blood vessels VS2, out of the observation targets, are shown is displayed in the second image. The second image is obtained on the basis of the second illumination light beam including violet light, blue light, green light, and red light. As shown in FIG. 12, in a case where the observation target is illuminated with the second illumination light beam, violet light V and blue light B of the second illumination light beam reach a deep layer where the deep blood vessels VS2 are distributed. Accordingly, a blue light image BP obtained on the basis of the reflected light of violet light V and blue light B includes an image of the deep blood vessels VS2. Here, since the light intensity of blue light B is higher than the light intensity of violet light V, the image obtained on the basis of the reflected light of violet light V and blue light B is referred to as a blue light image BP. Further, green light G and red light R of the second illumination light beam reach the background mucous membrane BM that is distributed at a position deeper than the positions of the superficial blood vessels VS1 and the deep blood vessels VS2 (blood vessels located at positions deeper than the positions of the superficial blood vessels VS1). Accordingly, a green and red light image GRP obtained on the basis of the reflected light of green light G and red light R includes an image of the background mucous membrane BM. As described above, since the second image is an image in which the blue light image BP and the green and red light image GRP are combined with each other, the image of the background mucous membrane BM and the deep blood vessels VS2 is displayed.

The image storage unit 56 performs image storage processing. The image storage processing is processing of storing an image, and processing of, for example, storing a first image and a second image selected from a plurality of the first images acquired by the image signal acquisition unit 51 and a plurality of the second images acquired by the image signal acquisition unit 51, respectively.

The storage control unit 61 controls the image storage processing. Specifically, when the processing start operation for starting the image storage processing is performed, the storage control unit 61 selects a first image and a second image that satisfy a preset selection condition from the plurality of first images and the plurality of second images acquired in the target period that is set so as to include the time when the processing start operation is performed, in order to store the first image and the second image in the storage unit 63, respectively.

The processing start operation in the image storage processing is, for example, a still image recording instruction (freeze instruction or release instruction) operation through the still image recording instruction portion 12f. In a case where the still image recording instruction is input by the operation of the still image recording instruction portion 12f, the processing start operation is performed and the image storage processing or the like is started, through the central control unit 59. The image storage unit 56 stores endoscopic images such as the first image and the second image selected by the preset selection condition in the storage unit 63 or a storage (not shown), under the control performed by the storage control unit 61. The storage is an external storage device connected to the processor device 16 through a local area network (LAN) or the like, and is, for example, a file server of a system for filing an endoscopic image, such as a picture archiving and communication system (PACS), or a network attached storage (NAS).

The target period setting performed by the storage control unit 61, the switching control between illumination light beams performed by the light source processor 21, and the like, in addition to the start of the image storage processing, are performed on the basis of the processing start operation. The target period is a period for deciding a target, in which the first image and the second image to be stored in the storage unit 63 are selected, and the first image and the second image to be stored in the storage unit 63 are selected from the plurality of first images and the plurality of second images acquired in this period. The target period includes the time when the processing start operation is performed. Further, the target period is preferably a period in which the image processor acquires a plurality of the first images which is a preset number and a plurality of the second images which is a preset number. As described above, the switching control between illumination light beams is a control in which the light source processor 21 switches, out of the first illumination light beam and the second illumination light beam, one being emitted to the other to emit the other in the target period.

Figure 13:
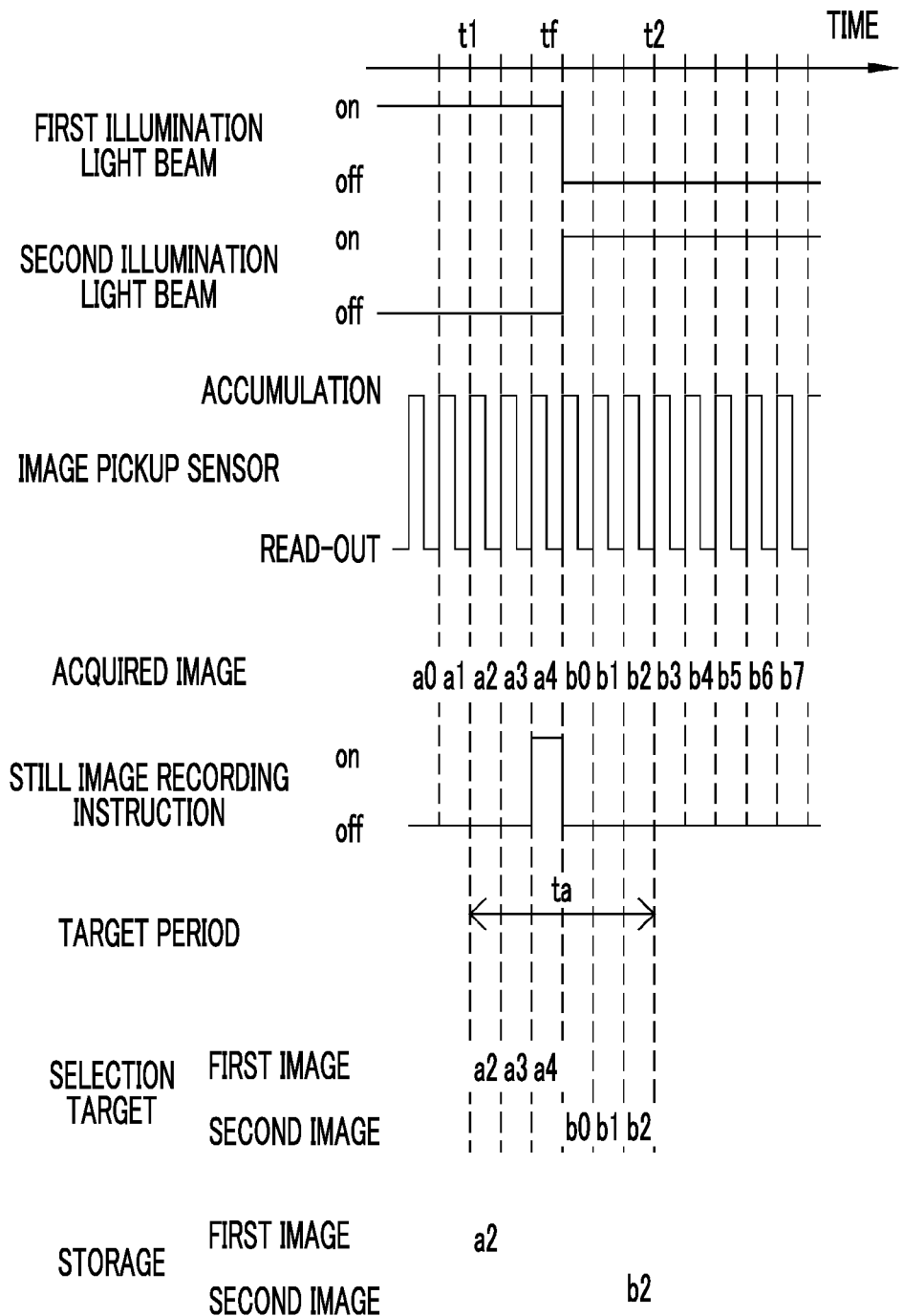
FIG. 13 is a diagram illustrating an example of storage of a still image in the first special observation mode.

As shown in FIG. 13, the image storage processing is specifically performed as follows. For example, in the first special observation mode, the first illumination light beam is continuously emitted as the illumination light beam (first period). The image pickup sensor 45 acquires image signals by performing charge accumulation and read-out for each frame. The acquired image signals are temporarily stored in the temporary storage unit 62. The temporary storage unit 62 always stores a fixed number of images set in advance. Therefore, for example, a first image a0 in a first frame shown in FIG. 13, a first image a1 in the next frame, a first image a2 in the next frame, and a first image a3 in the next frame are continuously temporarily stored until the type of illumination light beam is switched.

Here, in a case where the still image recording instruction is given at time tf by the operation of the still image recording instruction portion 12f, the still image recording instruction becomes the processing start operation of the image storage processing, and the setting of a target period ta, the switching between illumination light beams, the selection of images to be stored, and the storage of the selected images are performed. In the setting of the target period ta, since the target period ta includes a time when the still image recording instruction which is the processing start operation is given, and in the case of FIG. 13, the target period is preset to a period in which three first images and three second images are acquired, the target period is set to a period in which three first images and three second images are acquired, that is, a period of three frames for each image. Since the target period ta is a period in which both the first image and the second image can be acquired, the light source processor 21 switches, out of the first illumination light beam and the second illumination light beam, one being emitted to the other in a case where an illumination light beam being emitted is not switched in the target period ta. In the case of FIG. 13, since the first illumination light beam is emitted in the first special observation mode, the light source processor 21 switches the first illumination light beam to the second illumination light beam in response to the still image recording instruction.

The switched second illumination light beam is continuously emitted (second period). As in the acquisition of the first image, the image pickup sensor 45 acquires image signals by performing charge accumulation and read-out for each frame. A second image b0 in the first frame, a second image b1 in the next frame, and a second image b2 in the next frame are temporarily stored in the temporary storage unit 62. Since the image signal acquisition unit 51 acquires an image for each frame, for example, a second image b3 and a second image b4 are continuously temporarily stored until the type of illumination light beam is switched. Since the target period ta for temporary storage is set to be a period in which three first images and three second images are acquired, the start of the target period ta is time t1 that goes back by three frames from the time when the still image recording instruction is given, and the end point of the target period ta is time t2 advanced by three frames from the time when the still image recording instruction is given. Specifically, the target period ta is a period from time t1 to time t2, in which time tf when the still image recording instruction is given is sandwiched therebetween. At this point in time, the storage control unit 61 decides the first images a2, a3, and a4, and the second images b0, b1, and b2, as images acquired in the target period ta, and selects images to be stored in the storage unit 63, out of these images.

The storage control unit 61 selects, out of the plurality of first images and the plurality of second images stored by the temporary storage unit 62, a first image and a second image that satisfy the preset selection condition from the plurality of first images and the plurality of second images acquired in the target period ta, respectively. The preset selection condition is a condition that the first image and the second image to be stored are in a state suitable for comparison or superimposition. For example, the storage control unit 61 preferably sets the selection condition that a first image having the least blur out of the plurality of acquired first images or a second image having the least blur out of the plurality of acquired second images is selected.

As a method of selecting the first image having the least blur or the second image having the least blur, a known method can be used. For example, it is possible to select an image having the smallest amount of blur by calculating the amount of blur in each image. A method based on image analysis, a method based on the image pickup sensor 45, or the like is mainly used as a method of calculating the amount of blur, and there is a method of estimating a point spread function (PSF) for each of a plurality of regions in an image and estimating the direction and magnitude of blur from the point spread function with high accuracy, as the method based on image analysis (see JP5499050B, corresponding to U.S. Pat. No. 8,723,965B2). In addition, there is a method of detecting a movement vector from image signals and detecting the amount of blur of an image on the basis of the movement vector (see JP1991-16470A (JP-H03-16470A)). Further, a method of calculating a contrast and detecting an image having a large contrast as an image having a small amount of blur is also preferably used.

In FIG. 13, the first image a2 decided to have the least blur, out of the first images a2, a3, and a4, and the second image b2 decided to have the least blur, out of the second images b0, b1, and b2, are selected. The first image a2 and the second image b2 selected by the storage control unit 61 are stored in the storage unit 63 by the storage control unit 61. The image storage unit 56 uses the image signals sent from the signal processing unit 55 to perform image storage processing, and also sends the image signals to the display control unit 57 for display.

The image acquired by the image signal acquisition unit 51 or the image stored by the storage unit 63 has a time acquired as accessory information on the image, but it is preferable that the storage unit 63 stores the first image and the second image after adding information regarding the corresponding illumination light beams. In this case, it is preferable to have information, such as the type of illumination light beam, or information on the observation mode, as the accessory information. Further, for example, identification information or an identifier associated with the illumination light beam or the observation mode, such as a tag, may be added to the file name of the image. According to the above, it is possible to easily recognize at what time the acquired or stored image is the first image or the second image acquired.

The display control unit 57 performs control to display the image on the display 18, which is a display means. For example, the display control unit 57 performs control to continuously display the normal image as a moving image on the display 18 in the normal observation mode, to continuously display the first image or the second image as a moving image on the display 18 in the special observation mode, and to automatically switch any one of the first image or the second image to continuously display the switched image as a moving image on the display 18 in the multi-observation mode. Further, in a case where the still image recording instruction is given, the display control unit 57 performs control to display the endoscopic images such as the stored first image and the stored second image, as still images, on the display 18.

In a case where the still images such as the first image and the second image are displayed, the display control unit 57 displays the still images in a display method set according to the purpose. Examples of the display method include a method of displaying the still images side by side on the display 18, a method of adjusting the transparency of each image to superimpose and display the still images, or a method of switching between the still images in a short time of 1 second or less on the same region of the display 18 to display the still images like an animation.

The video signal generation unit 58 converts the normal image and the special image, which are output from the display control unit 57, or the first image and the second image, which are stored in the storage unit 63 into video signals that allow full-color display on the display 18. The video signals that have been converted are input to the display 18. With this, the normal image, the special image, the accessory information, or the like is displayed on the display 18.

As described above, with the endoscope system 10 having the above configuration, the switching to the different type of illumination light beam, the selection of images for respective types of illumination light beams, and the storage of the plurality of selected images are performed by a single operation of the still image recording instruction portion 12f, while performing observation using the desired illumination light beam. Since selection is performed on the basis of the preset selection condition, it is possible to select and store appropriate images according to the purpose, for example, images between which a difference in time caused by the plurality of types of illumination light beams is small or images having less blur. Accordingly, with the endoscope system 10, it is possible to store a plurality of types of still images corresponding to a plurality of illumination light beams in a state suitable for comparison or superimposition, through a single instruction.

Figure 14:
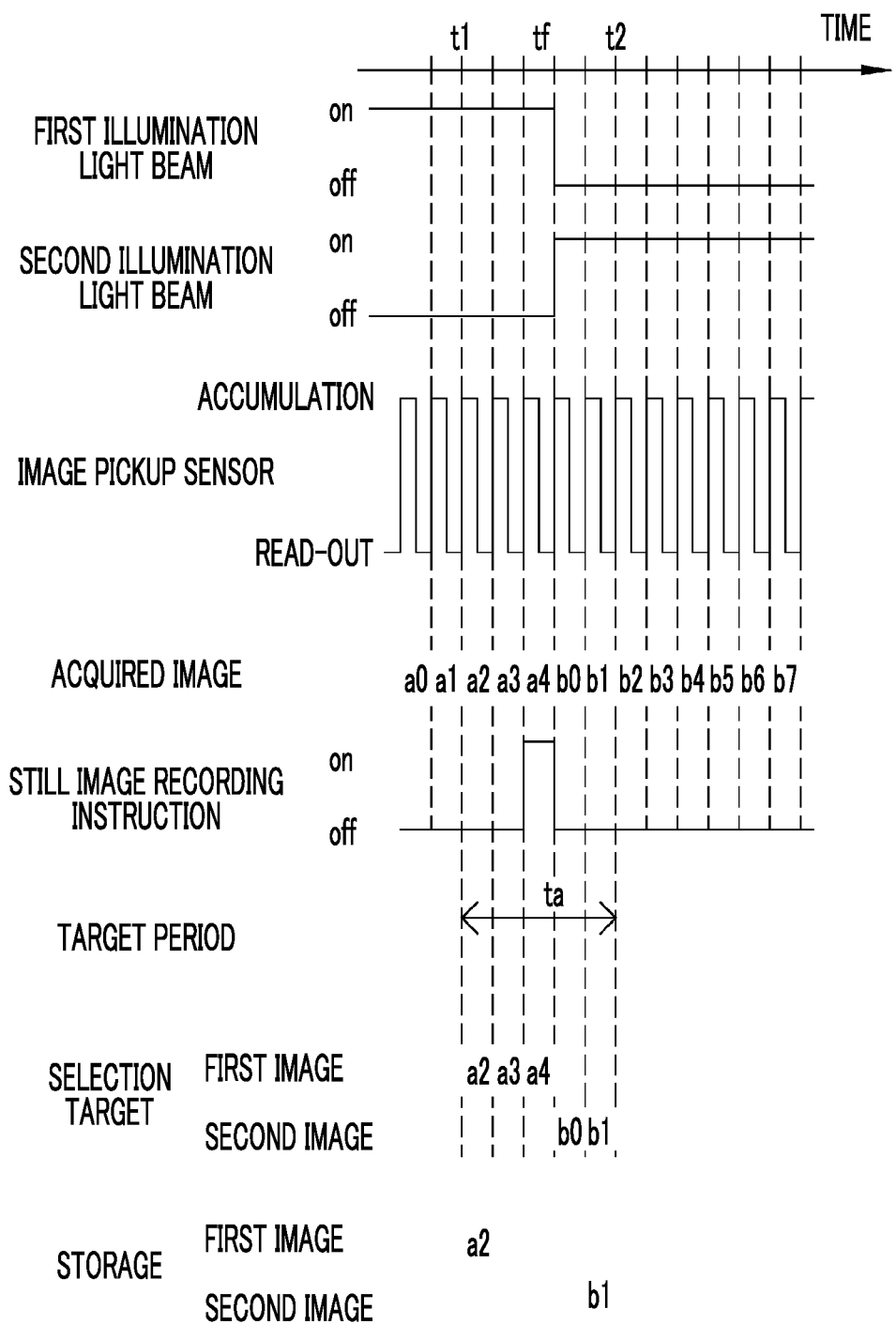
FIG. 14 is a diagram illustrating another example of the storage of the still image in the first special observation mode.

The target period may be a period in which the image processor acquires the first image and the second image that satisfy the selection condition. Therefore, for example, the target period may be a period up to the point in time when the first image and the second image that satisfy the selection condition can be acquired. Specifically, as shown in FIG. 14, in a case where the illumination light beams or the like are the same as in FIG. 13, the storage control unit 61 selects the first image a2, and then selects the second image b1 in a case where the second image b0 does not satisfy the selection condition but the second image b1 satisfies the selection condition, and ends the target period ta. Therefore, the storage control unit 61 stores the first image a2 and the second image b1. As soon as the first image or the second image is stored in the temporary storage unit 62, the storage control unit 61 checks whether the image satisfies the preset selection condition for each image, and selects the image satisfying the selection condition. Further, in this case, the target period ta from time t1 to time t2 is shorter by one frame than in the case of FIG. 13. The above configuration is preferable because the period for storing the first image and the second image can be shortened.

The light source processor 21 may alternately switch and emit the first illumination light beam and the second illumination light beam at a preset cycle. Further, it is preferable to use a combination of illumination light beams with which the obtained first and second images have the same base color tone. The base color tone is a color tone that is a base in an endoscopic image, and is, for example, a color tone that occupies a large proportion of an area in the endoscopic image. In a case where the base color tone is the same even for different endoscopic images, the overall color tone does not differ significantly when compared, and it is easy to recognize the difference in parts other than the base color tone. In the first image using the first illumination light beam and the second image using the second illumination light beam as described above, examples of obtaining observation images of which the base color tones have natural color tones include performing white balance processing by using a specific gain coefficient through the DSP 52. This base color tone is referred to as a first base color tone.

It is assumed that the specific gain coefficient in a case where the first base color tone is obtained is corrected by using the endoscopic image acquired in the past. For example, in the first image, the gain coefficient is corrected in the subsequent first image by using the second image.

Further, in the second image, the gain coefficient is corrected in the subsequent second image by using the first image.

As described above, the first illumination light beam is set as an illumination light beam that enhances the superficial blood vessels, and the second illumination light beam is set as an illumination light beam that enhances the medium-depth layer blood vessels, and the first illumination light beam and the second illumination light beam are automatically switched at a fixed cycle. With this, since the base color tones are the same first base color tone, the color tone of the part having a large proportion of the area in the endoscopic image does not change, and only the different part is enhanced and displayed. Accordingly, since the superficial blood vessels and the medium-depth blood vessels of the same observation target are enhanced and displayed like an animation, the blood vessel information in the depth direction can be obtained in an easy-to-see state.

Figure 15:
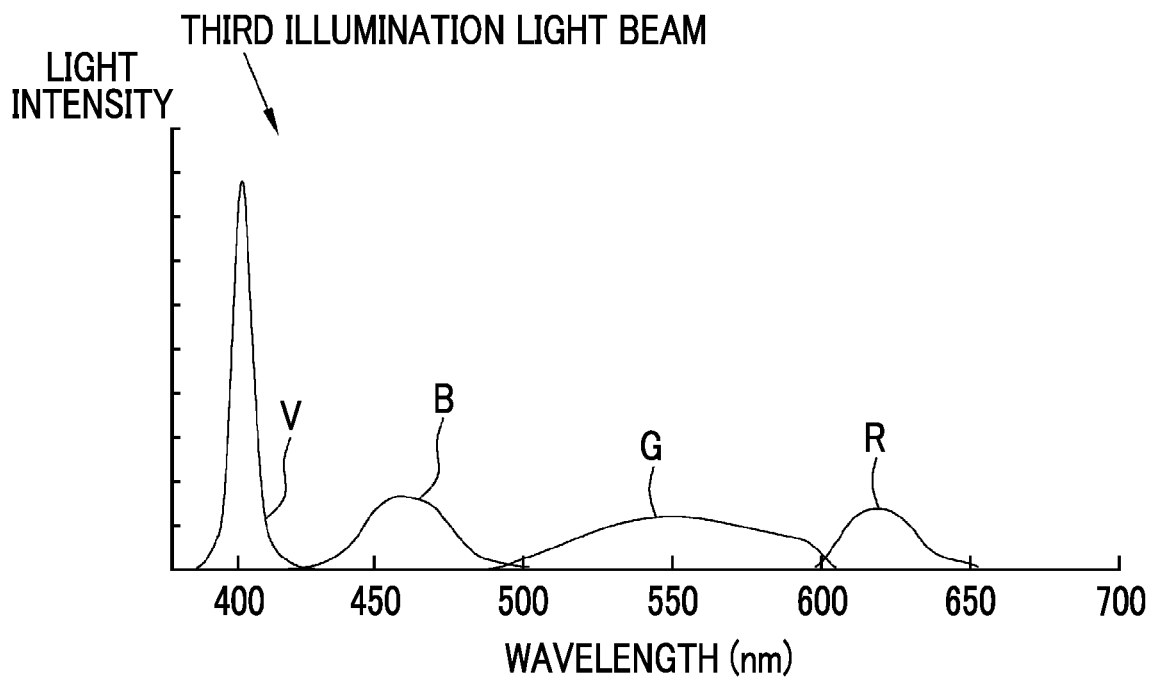
FIG. 15 is a graph showing a spectrum of a third illumination light beam.

Further, it is also preferable to use a combination of a third illumination light beam and a fourth illumination light beam by using the third illumination light beam instead of the above-described first illumination light beam and the fourth illumination light beam instead of the second illumination light beam, as illumination light beams. The light source processor 21 controls the respective LEDs 20a to 20d such that the third illumination light beam of which the light intensity ratios between violet light V, blue light B, green light G, and red light R are Vs3:Bs3:Gs3:Rs3 is emitted. The light intensity ratios Vs3:Bs3:Gs3:Rs3 correspond to the light amount condition of the third illumination light beam. It is preferable that the third illumination light beam enhances superficial blood vessels. For this purpose, it is preferable that the light intensity of violet light V of the third illumination light beam is set to be higher than the light intensity of blue light B. For example, as shown in FIG. 15, the ratio between the light intensity Vs3 of violet light V and the light intensity Bs3 of blue light B is set such that the light intensity Vs3 of violet light V is high.

Figure 16:
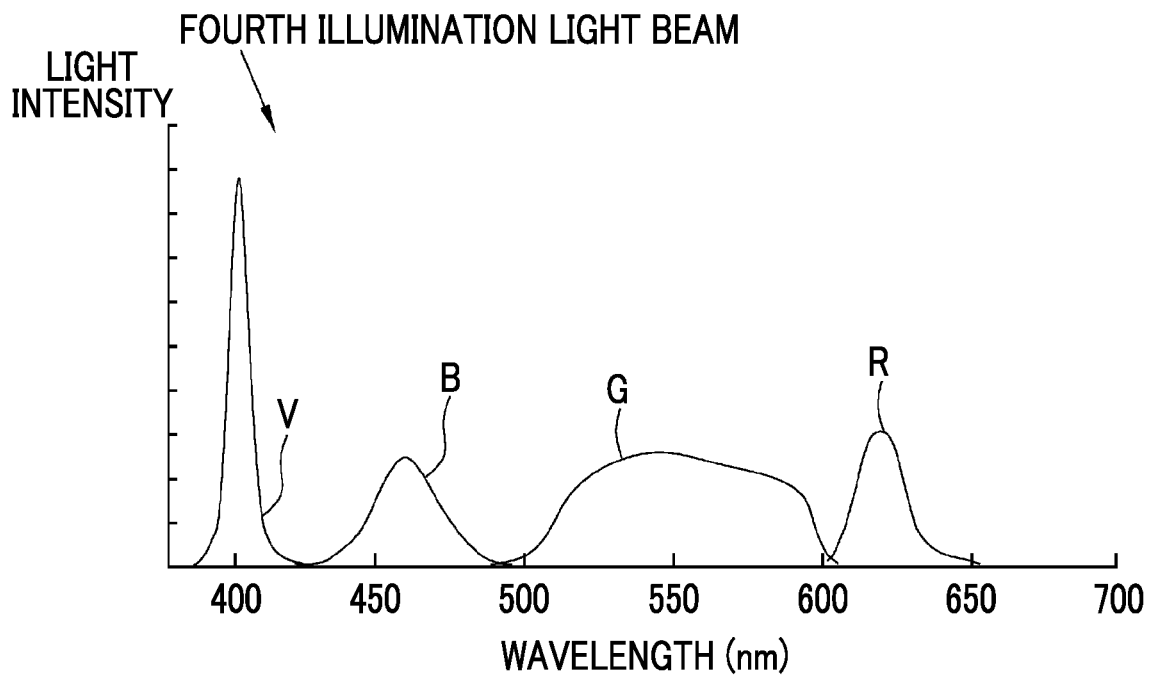
FIG. 16 is a graph showing a spectrum of a fourth illumination light beam.

Further, the light source processor 21 controls the respective LEDs 20a to 20d such that the fourth illumination light beam of which the light intensity ratios between violet light V, blue light B, green light G, and red light R are Vs4:Bs4:Gs4:Rs4 is emitted. The light intensity ratios Vs4:Bs4:Gs4:Rs4 correspond to the light amount condition of the fourth illumination light beam. It is preferable that the fourth illumination light beam enhances the superficial blood vessels and makes the image bright even in a distant view. For this purpose, it is preferable that the light intensity of blue light B, the light intensity of green light G, and the light intensity of red light R in the fourth illumination light beam are set to be slightly higher than the respective light intensities in the third illumination light beam. For example, as shown in FIG. 16, the ratios between the light intensity Bs4 of blue light B, the light intensity Gs4 of green light G, and the light intensity Rs4 of red light R are set to be slightly higher than the respective light intensities in the third illumination light beam.

The endoscopic images obtained by the third illumination light beam and the fourth illumination light beam have the same base color tone, that is, a second base color tone. The endoscopic image having the second base color tone is an endoscopic image having a color tone with a small amount of red component, in which the structure of the mucous membrane surface layer, for example, microvessels are enhanced. The third illumination light beam is set as an illumination light beam that enhances the superficial blood vessels, and the fourth illumination light beam is set as an illumination light beam that enhances the superficial blood vessels and that makes the image bright even in a distant view, and the third illumination light beam and the fourth illumination light beam are automatically switched at a fixed cycle. With this, since the base color tones are the second base color tone, the color tone of the part having a large proportion of the area in the endoscopic image does not change, and only the different part is enhanced and displayed. Accordingly, since the subtle differences between the superficial blood vessels of the same observation target are enhanced and displayed like an animation, microvessel information in the superficial blood vessels can be obtained in an easy-to-see state.

The light source processor 21 may perform control to switch, out of the first illumination light beam and the second illumination light beam, one which is emitted before the processing start operation to the other to emit the other, in a case where the processing start operation is performed after a preset period starting from the time when light emission is switched between the first illumination light beam and the second illumination light beam. The preset period starting from the time when light emission is switched between the first illumination light beam and the second illumination light beam is defined as a post-switching period. Although it is not important whether light emission is switched between the first illumination light beam and the second illumination light beam because the user switches between the observation modes or because the light source processor 21 periodically switches between the illumination light beams in the multi-observation mode, the light source processor 21 switches and emits illumination light beams through the processing start operation in a case where the processing start operation is performed after the post-switching period starting from the time when light emission is switched between the illumination light beams is passed. Therefore, the target period ta in this case need only be set on the basis of the processing start operation.

Figure 17:
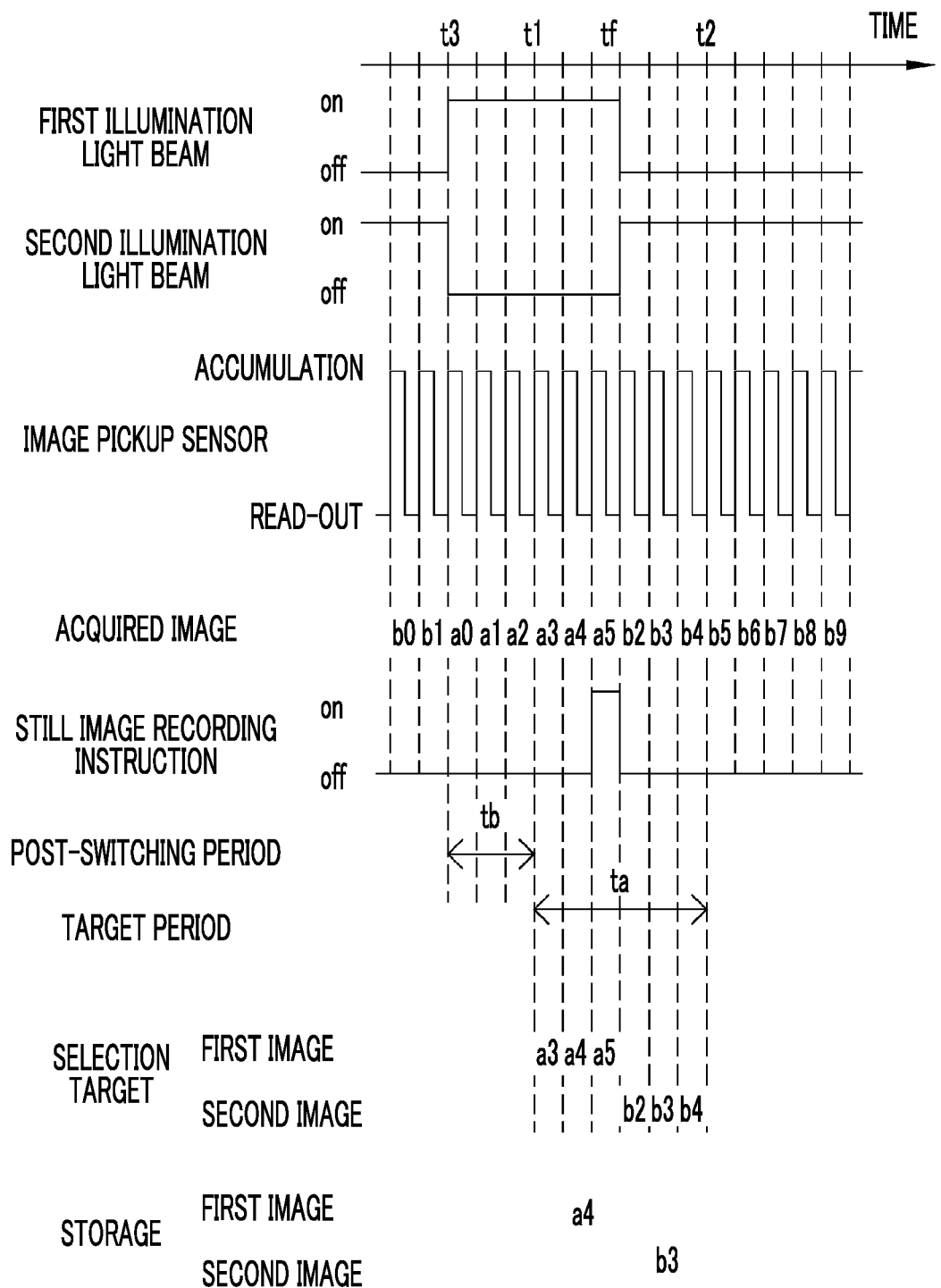
FIG. 17 is a diagram illustrating an example of storage of a still image in a case where a processing start operation is performed after a post-switching period.

Specifically, as shown in FIG. 17, in a case where the second illumination light beam is switched to the first illumination light beam at time t3, a post-switching period tb starts at time t3, and the post-switching period tb ends at time t1 because, for example, the post-switching period tb corresponds to three frames. Since time tf of the still image recording instruction is after time t1 when the post-switching period tb ends is passed, the light source processor 21 performs control to switch the first illumination light beam which is emitted before the processing start operation of the image storage processing to the second illumination light beam to emit the second illumination light beam in response to the still image recording instruction. The post-switching period tb is preferably, for example, a period equal to or longer than the number of frames corresponding to the number of endoscopic images acquired for one type of illumination light beam in the target period ta. In the case of FIG. 17, since the number of endoscopic images acquired for one type of illumination light beam in the target period ta is three, the post-switching period tb is set to three frames. With the above configuration, the switching between the illumination light beams is performed in the target period ta, so that the difference in time between the first image and the second image as selection targets can be made smaller.

Figure 18:
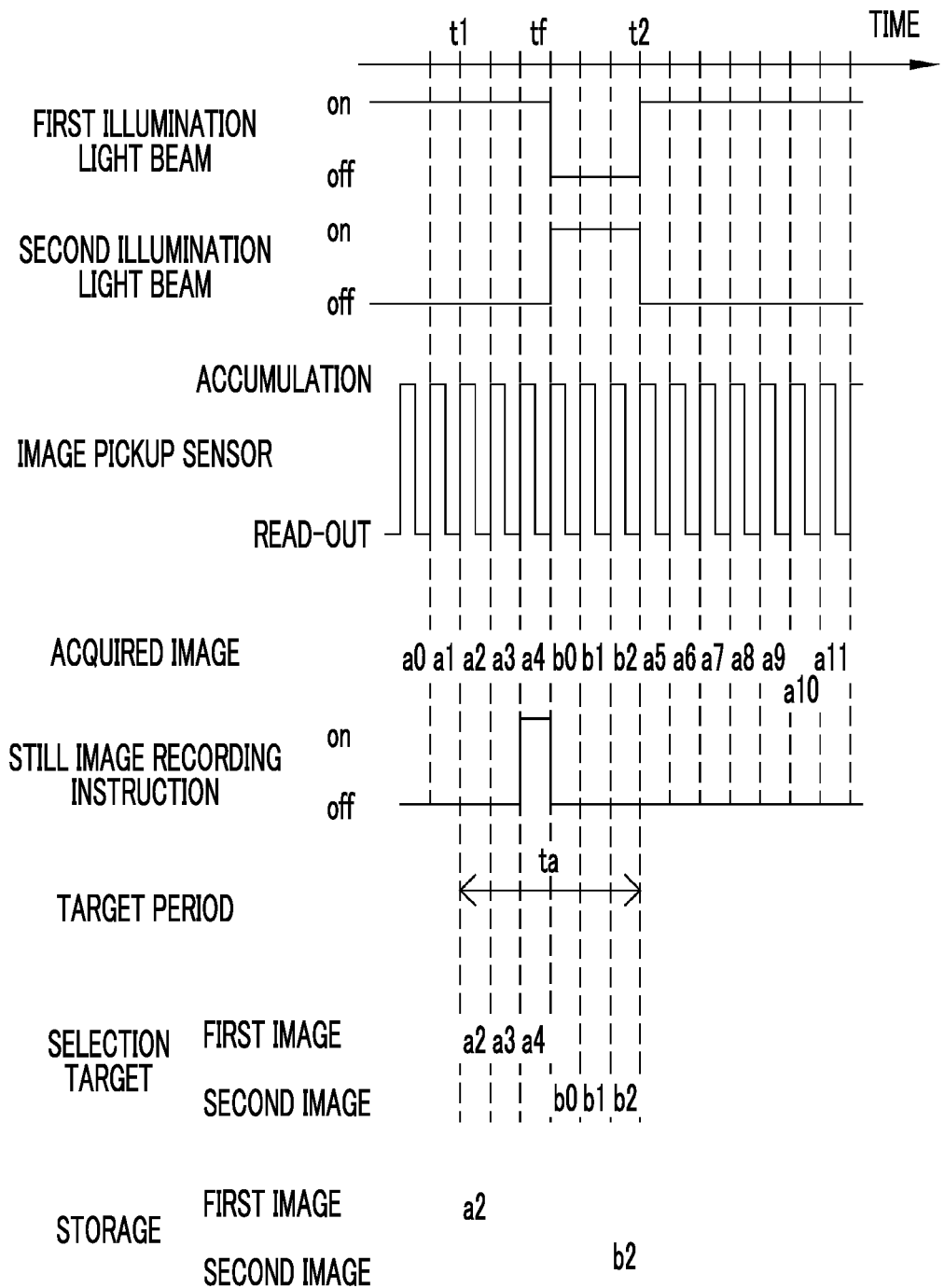
FIG. 18 is a diagram illustrating an example of storage of a still image in a case of performing light emission by switching between illumination light beams when a target period is passed.

Further, the light source processor 21 may perform control to switch, out of the first illumination light beam and the second illumination light beam, one which is emitted after the processing start operation to the other to emit the other, when the target period ta is passed. Specifically, as shown in FIG. 18, since the processing start operation is the still image recording instruction, the light source processor 21 performs control to switch the second illumination light beam which is emitted after the still image recording instruction to the first illumination light beam which is emitted before the still image recording instruction to emit the first illumination light beam when time t2 which is the end point of the target period ta is passed. The target period ta may be a period in which the image processor acquires a plurality of the first images which is a preset number and a plurality of the second images which is a preset number, or a period in which the image processor acquires a first image and a second image that satisfy the selection condition.

With the above configuration, for example, in a case where the observation target is observed in the first special observation mode, the still image recording instruction is given once, so that it is possible to automatically store images using different illumination light beams, such as the first image and the second image, and the switching to the second illumination light beam is limited to the required period. Accordingly, the user can obtain different types of still images while continuing the observation in the mode the user is observing.

Further, the light source processor 21 may perform control to switch, out of the first illumination light beam and the second illumination light beam, one which is emitted after the processing start operation to the other to emit the other, when a preset period starting from the time of the processing start operation is passed. The preset period starting from the time of the processing start operation is defined as a post-processing start operation period. The target period ta in this case need only be set on the basis of the processing start operation.

Figure 19:
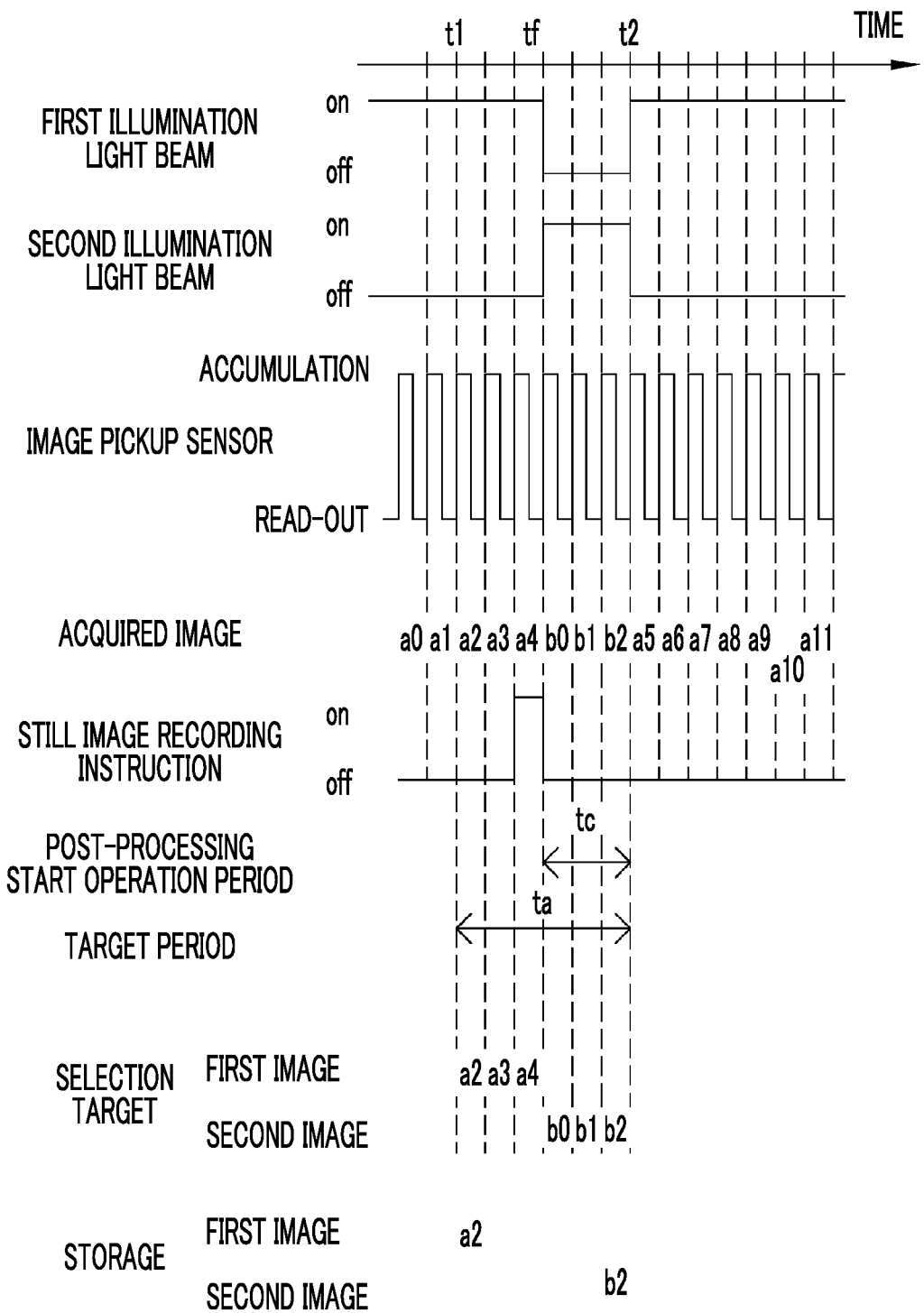
FIG. 19 is a diagram illustrating an example of storage of a still image in a case of performing light emission by switching between illumination light beams when a post-processing start operation period is passed.

Specifically, as shown in FIG. 19, since the processing start operation of the image storage processing is the still image recording instruction, the light source processor 21 performs control to switch the second illumination light beam which is emitted after the still image recording instruction to the first illumination light beam which is emitted before the still image recording instruction to emit the first illumination light beam, at time t2 when a post-processing start operation period tc is passed from time tf of the still image recording instruction. The post-processing start operation period tc is preferably, for example, a period equal to or longer than the number of frames corresponding to the number of endoscopic images acquired for one type of illumination light beam in the target period ta. In the case of FIG. 19, since the number of endoscopic images acquired for one type of illumination light beam in the target period ta is three, it is preferable to lengthen the post-processing start operation period tc to three frames or more. Therefore, in FIG. 19, the post-processing start operation period tc is set to three frames.

With the above configuration, for example, in a case where the observation target is observed in the first special observation mode, the still image recording instruction is given once, so that it is possible to automatically store images using different illumination light beams, such as the first image and the second image, and the switching to the second illumination light beam is limited to the set required period. Accordingly, the user can more reliably obtain different types of still images, such as the first image and the second image as selection targets, in a state in which a difference in time therebetween is small while continuing the observation in the mode the user is observing.

Further, the light source processor 21 may perform control to emit, out of the first illumination light beam and the second illumination light beam, one which is emitted before the processing start operation even after the processing start operation, in a case where the processing start operation is performed in a preset period starting from a time when light emission is switched between the first illumination light beam and the second illumination light beam. That is, in a case where the processing start operation is performed within the post-switching period tb, the illumination light beam is not switched in response to the processing start operation, and the illumination light beam which is emitted at the time of the processing start operation is extended. The target period ta in this case need only include a light emission period of the illumination light beam before the switching.

Figure 20:
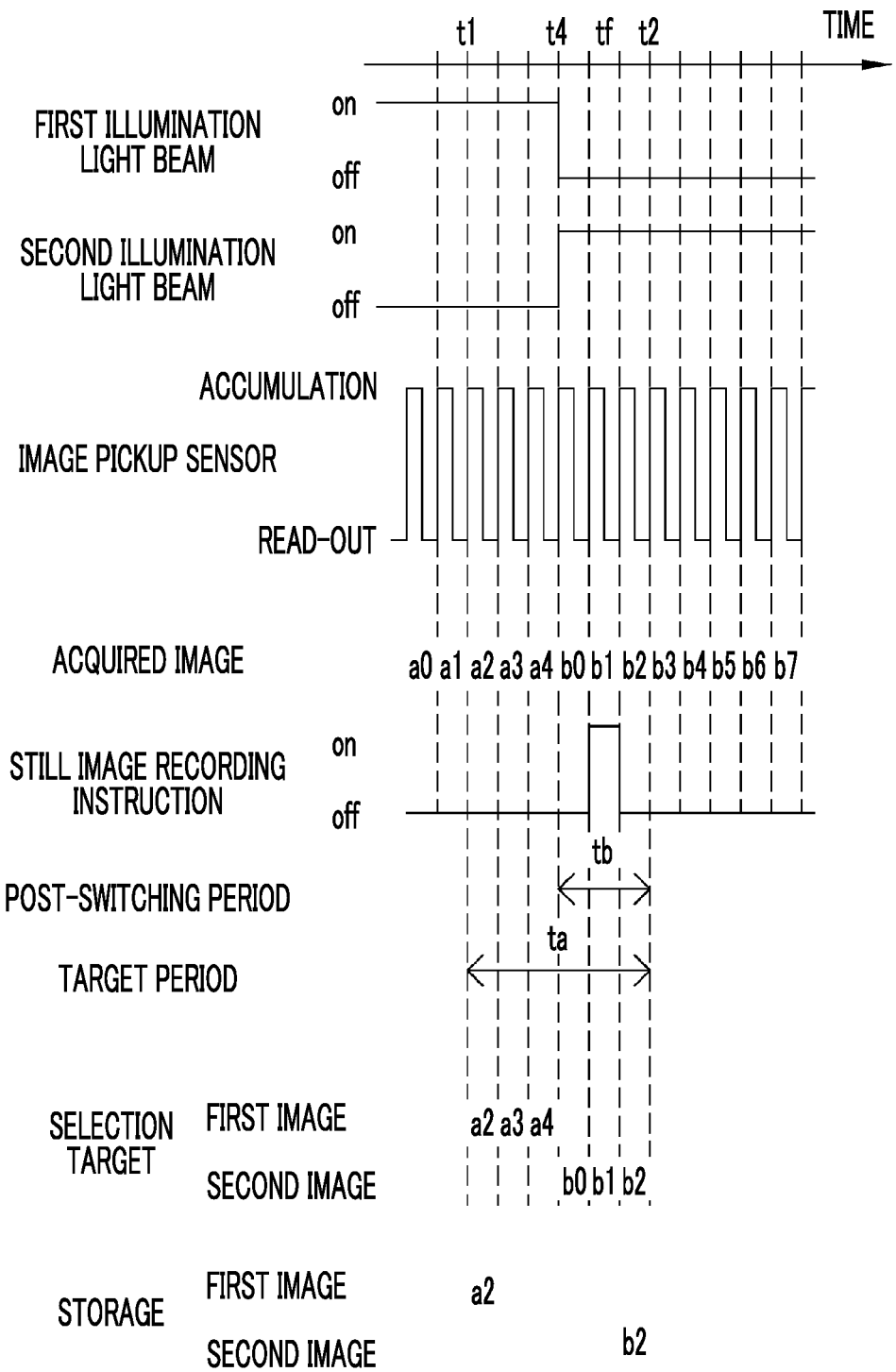
FIG. 20 is a diagram illustrating an example of storage of a still image in a case where the processing start operation is performed in the post-switching period.

Specifically, as shown in FIG. 20, in a case where the light source processor 21 switches the illumination light beam at time t4, for example, by periodically switching between the illumination light beams in the multi-observation mode, when the still image recording instruction is given at time tf, the still image recording instruction is given within the post-switching period tb because the post-switching period tb is set to the period of three frames from time t4 to time t2. In this case, the light source processor 21 does not switch between the illumination light beams even in a case where the still image recording instruction is given, and the target period ta is set on the basis of the switching between the illumination light beams at time t4. Therefore, the storage control unit 61 sets the target period ta to a period from time t1 to time t2 including the period before the switching between the illumination light beams. The post-switching period tb is the same as described above, and is set to three frames.

With the above configuration, the difference in time between the first image and the second image as selection targets can be more reliably made smaller, and it is possible to restrain the flicker of the images displayed on the display 18 caused by the frequent switching between illumination light beams and to restrain the occurrence of the problem of photosensitivity.

Furthermore, the light source processor 21 may perform control to switch, out of the first illumination light beam and the second illumination light beam, one which is emitted at the time of the processing start operation to the other to emit the other, after a preset period starting from the time when the light emission is switched between the first illumination light beam and the second illumination light beam, that is, the post-switching period tb, is passed. The target period ta in this case need only be set on the basis of the time when the light emission is switched between the first illumination light beam and the second illumination light beam.

Figure 21:
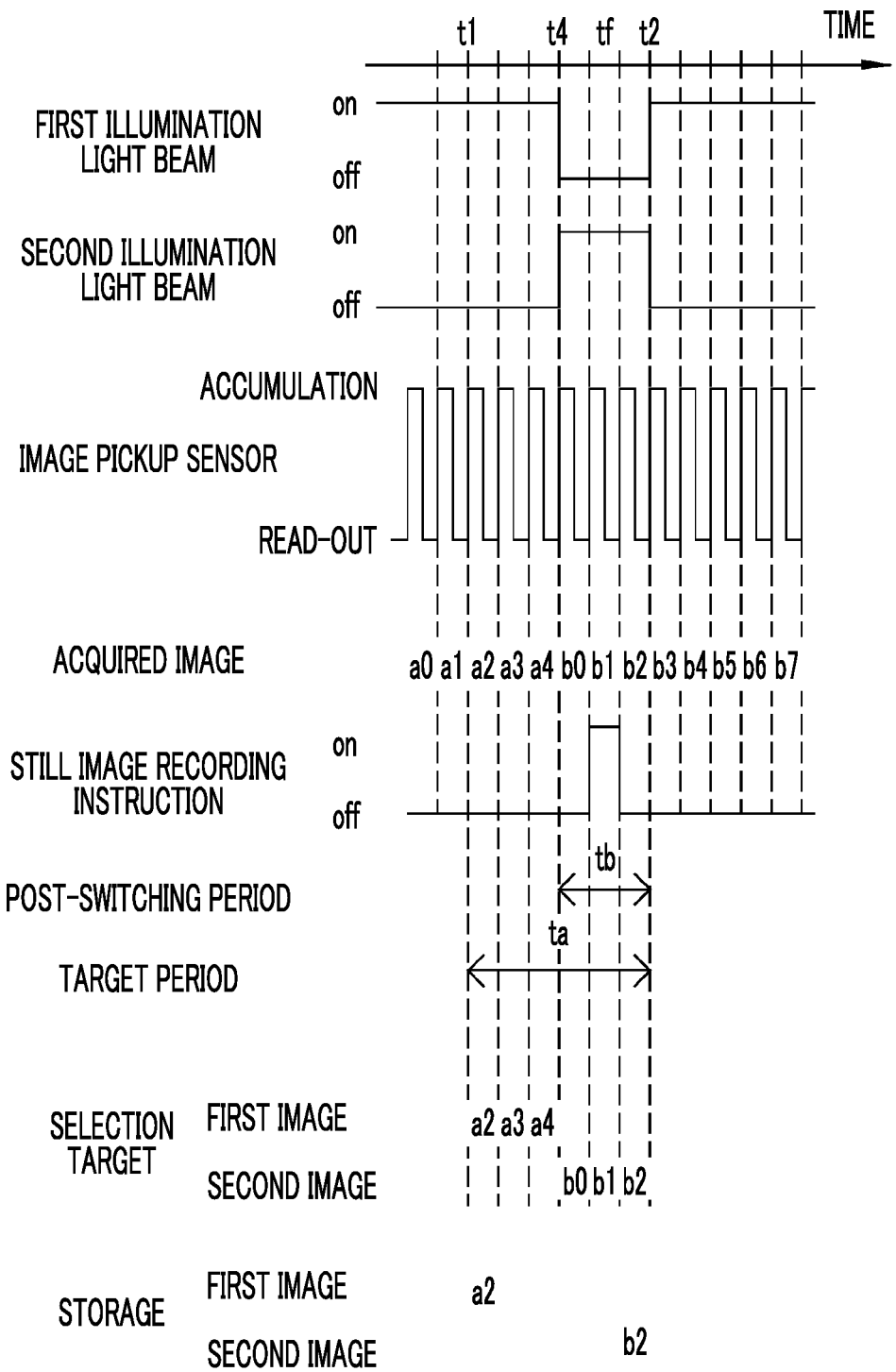
FIG. 21 is a diagram illustrating an example of a case of performing light emission by switching an illumination light beam to the first illumination light beam which is emitted before switching between illumination light beams, after the post-switching period is passed.

Specifically, as shown in FIG. 21, since the processing start operation of the image storage processing is the still image recording instruction, the light source processor 21 performs control to switch the second illumination light beam which is emitted at the time of the still image recording instruction to the first illumination light beam which is emitted before the light emission is switched between the first illumination light beam and the second illumination light beam, at time t2 when the post-switching period tb starting from time t4 when the light emission is switched between the first illumination light beam and the second illumination light beam is passed. The post-switching period tb is preferably, for example, a period equal to or longer than the number of frames corresponding to the number of endoscopic images acquired for one type of illumination light beam in the target period ta. In the case of FIG. 21, since the number of endoscopic images acquired for one type of illumination light beam in the target period ta is three, it is preferable to lengthen the post-switching period tb to three frames or more. Therefore, in the case of FIG. 21, the post-switching period tb is set to three frames.

Further, the light source processor 21 may perform control to switch, out of the first illumination light beam and the second illumination light beam, one which is emitted at the time of the processing start operation to the other to emit the other, after a preset period starting from the time of the processing start operation, that is, the post-processing start operation period tc, is passed. The target period ta in this case need only be set on the basis of the time when the light emission is switched between the first illumination light beam and the second illumination light beam.

Figure 22:
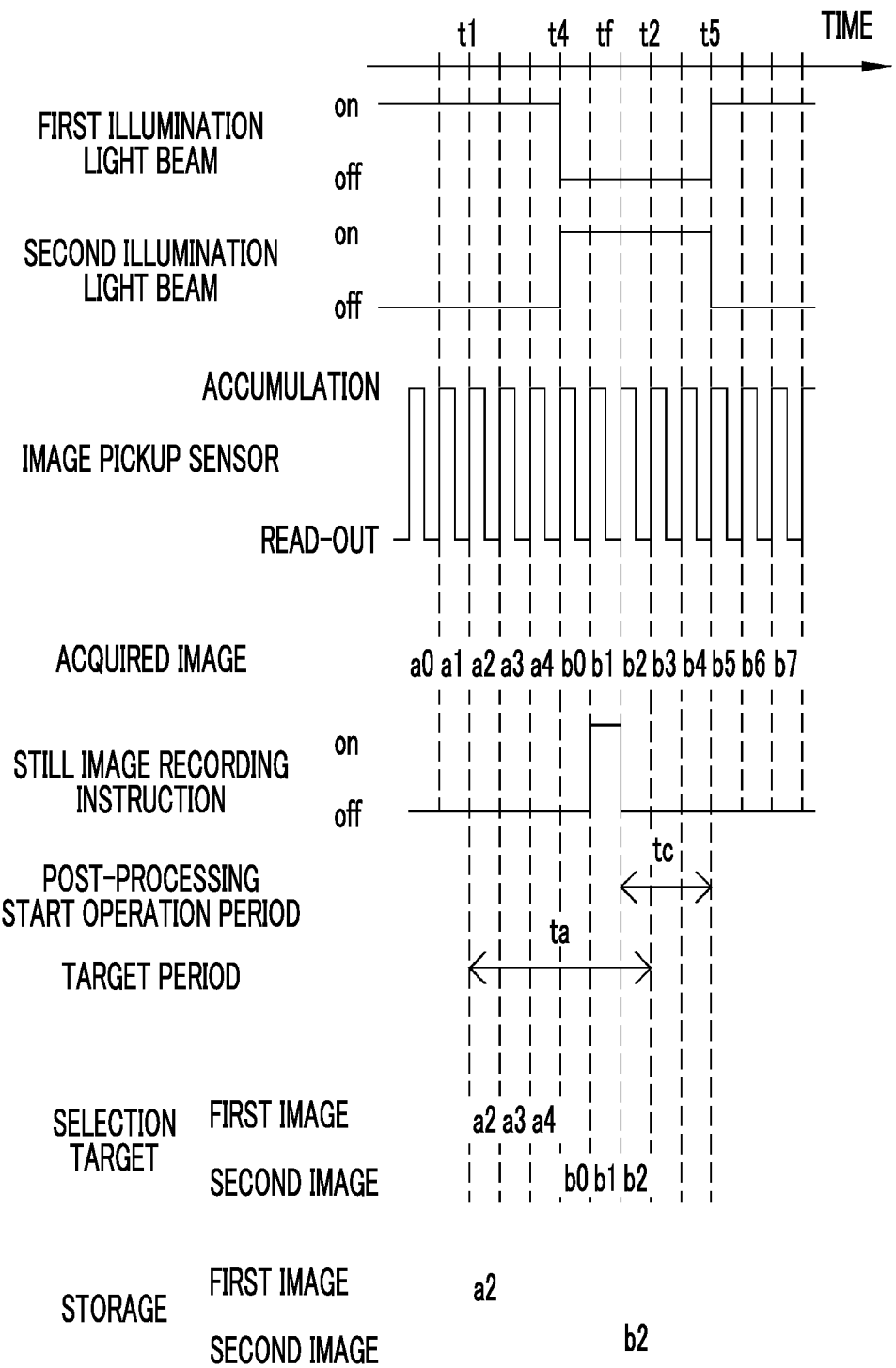
FIG. 22 is a diagram illustrating another example of the case of performing light emission by switching an illumination light beam to the first illumination light beam which is emitted before switching between illumination light beams, after the post-processing start operation period is passed.

Specifically, as shown in FIG. 22, since the processing start operation of the image storage processing is the still image recording instruction, the light source processor 21 performs control to switch the second illumination light beam which is emitted at the time of the still image recording instruction to the first illumination light beam which is emitted before the light emission is switched between the first illumination light beam and the second illumination light beam, at time t5 when the post-processing start operation period tc starting from time tf of the still image recording instruction is passed. The post-processing start operation period tc is preferably, for example, a period equal to or longer than the number of frames corresponding to the number of endoscopic images acquired for one type of illumination light beam in the target period ta. In the case of FIG. 22, since the number of endoscopic images acquired for one type of illumination light beam in the target period ta is three, it is preferable to lengthen the post-processing start operation period tc to three frames or more. Therefore, in FIG. 22, the post-processing start operation period tc is set to three frames.

With the above configuration, for example, in a case where the observation target is observed in the multi-observation mode, it is possible to restrain the flicker of images displayed on the display 18 caused by the frequent switching between illumination light beams, and to restrain the occurrence of the problem of photosensitivity, even in a case where the light source processor 21 automatically switches between illumination light beams regardless of the still image recording instruction. Further, the still image recording instruction is given once, so that it is possible to more reliably obtain different types of still images, such as the first image and the second image as selection targets, in a state in which a difference in time therebetween is small. Accordingly, the user can more reliably obtain different types of still images, such as the first image and the second image as selection targets, in an appropriate state, for example, while continuing the observation in the multi-observation mode the user is observing.

The preset selection condition may be a condition that a first image and a second image having the smallest positional deviation between the first image selected from the plurality of acquired first images and the second image selected from the plurality of acquired second images are selected. The positional deviation between the selected first and second images is small, so that it is possible to store the first image and the second image in a state suitable for comparison or superimposition.

As a method of selecting the first image and the second image having the smallest positional deviation therebetween, a known method can be used. Examples of the method based on image analysis include a method of dividing the first image and the second image and comparing and obtaining the cumulative amounts of the G image signals of the first image and the G image signals of the second image having similar signal characteristics in respective regions.

The preset selection condition may be a condition that a first image and a second image having a smallest difference in brightness between the first image selected from the plurality of acquired first images and the second image selected from the plurality of acquired second images are selected. The difference in brightness between the selected first and second images is small, so that it is possible to store the first image and the second image in a state suitable for comparison or superimposition.

As a method of selecting the first image and the second image having the smallest difference in brightness therebetween, a known method can be used. For example, brightness Y is calculated for each image, and a combination having the smallest difference in brightness Y is selected from the plurality of first images and the plurality of second images acquired in the target period ta. As a method of calculating the brightness Y, a known method can be used, and the brightness Y is set according to the purpose. For example, in a case where the brightness Y is calculated from the image signals of each image, the brightness Y may be calculated by the brightness $Y=\alpha \times R+\beta \times G+\gamma \times B$. Here, "R" represents the pixel value of the R image signal of each image, "G" represents the pixel value of the G image signal, and "B" represents the pixel value of the B image signal. Further, "$\alpha$, $\beta$, and $\gamma$" each represent a certain coefficient.

Further, the storage control unit 61 preferably sets the selection condition that a first image and a second image having a smallest difference in acquisition time between the first image selected from the plurality of acquired first images and the second image selected from the plurality of acquired second images are selected. The smaller the difference in acquisition time between the selected first and second images is, for example, the less likely it is that the blur of the first image or the blur of the second image, the positional deviation between the first image and the second image, the difference in brightness between the first image and the second image, and the like occur, so that it is possible to store the first image and the second image in a state suitable for comparison or superimposition.

The preset selection condition exemplified above may be used alone or in combination of two or more. In a case where the plurality of selection conditions is used in combination, images can be selected on the basis of the rate of match between the first image and the second image calculated by combining the plurality of selection conditions.

The rate of match can be, for example, the sum of the amount of blur and the amount of movement (the amount of positional deviation) between the selected first and second images. Specifically, first, out of the plurality of first images acquired in the target period ta, a first image having the smallest amount of blur is selected. Then, out of the plurality of second images acquired in the target period ta, a second image having the smallest amount of blur is selected. After that, out of the selected second images, a second image having the minimum amount of movement with respect to the selected first image is selected and stored. In this case, it is assumed that the smaller the amount of movement is, the higher the rate of match is.

Figure 23:
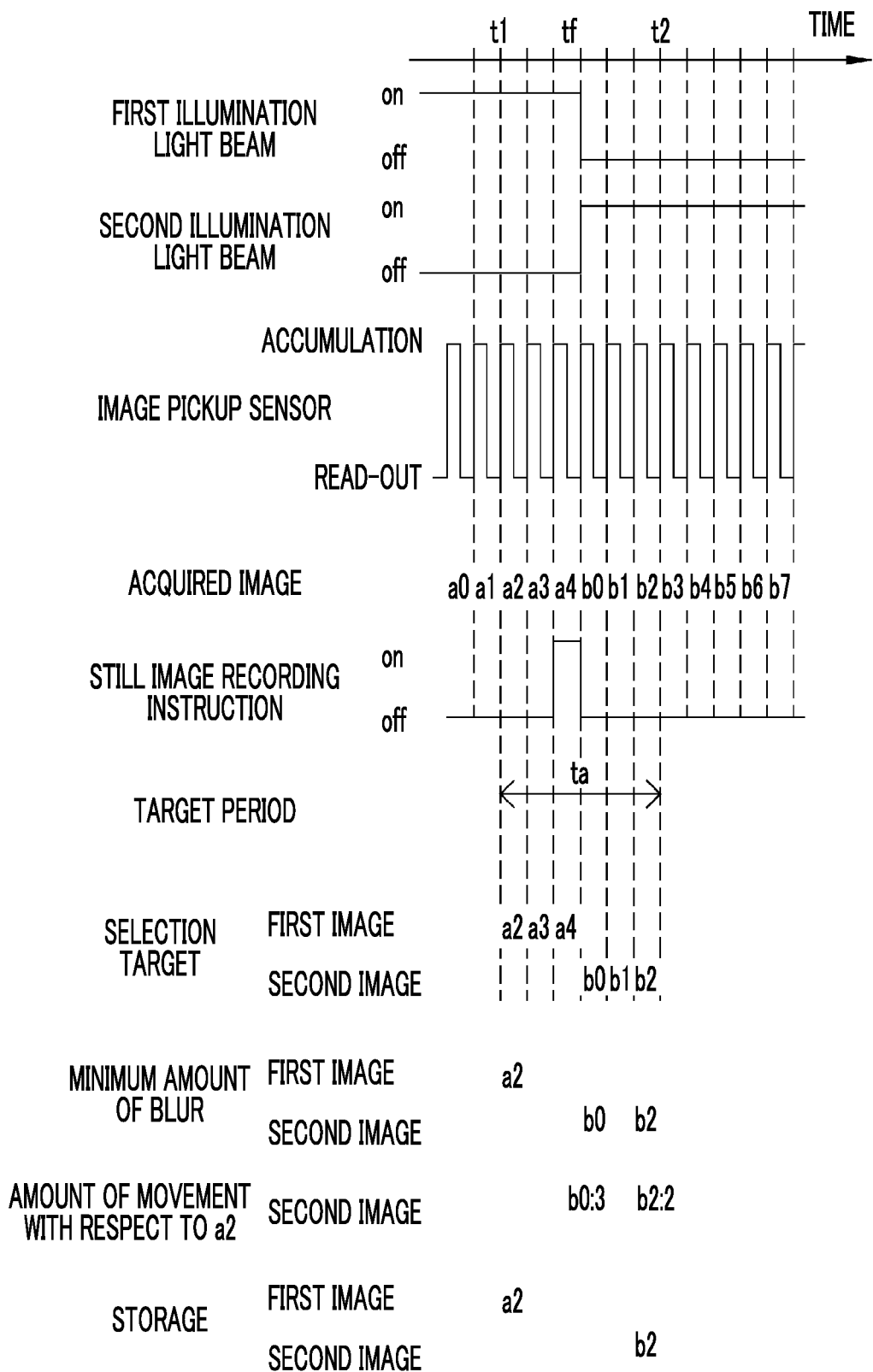
FIG. 23 is a diagram illustrating a selection condition and a stored endoscopic image.

As shown in FIG. 23, in a case where the selection targets are the first images a2, a3, and a4 and the second images b0, b1, and b2, the amount of blur is calculated in the first images a2, a3, and a4 and the first image a2 having the smallest amount of blur is selected, and the amount of blur is calculated in the second images b0, b1, and b2 and the second images b0 and b2 having the smallest amount of blur are selected. After that, the amount of movement from the first image a2 is calculated for the second images b0 and b2. In a case where the amount of movement with respect to the first image a2 is calculated to be 3 for the second image b0 and is calculated to be 2 for the second image b2, the first image a2 and the second image b2 are stored.

Further, the rate of match may be decided, for example, by calculating the amount of movement as described above for all of the plurality of first images and the plurality of second images obtained in the target period ta. After that, the pair of the first image and the second image, which corresponds to the case where the calculated value is the smallest, is selected and stored. The smaller the calculated value is, the higher the rate of match is.

As shown in FIG. 24, in a table 71, in a case where the selection targets are the first images a2, a3, and a4 and the second images b0, b1, and b2, the amount of blur is calculated for each of the first images a2, a3, and a4 and the second images b0, b1, and b2. The amount of blur in each image is the numerical value in parentheses. After that, the amounts of movement from the first images a2, a3, and a4 are calculated for the respective second images b0, b1, and b2. In the table 71, the subtotal of the amount of blur between the first image and the second image and the amount of movement between the first image and the second image are described in the columns of "amount of blur, amount of movement", respectively. The value obtained by adding the amount of blur and the amount of movement is described in the column of "total". In this way, nine total values are calculated in three first images and three second images.

In the table 71, the amount of blur of each image is as shown in parentheses, the amount of blur of the first image a2 is 3, the amount of blur of the first image a3 is 2, and the amount of blur of the first image a4 is 4. Further, the amount of blur of the second image b0 is 2, the amount of blur of the second image b1 is 3, and the amount of blur of the second image b2 is 1. At the portion intersecting the first image a2 and the second image b0 in the table 71, it is described that the subtotal of the amount of blur between the first image a2 and the second image b0 is 5, and that the amount of movement (positional deviation) calculated from the first image a2 and the second image b0 is 3. Further, in the column of total in this portion, it is described that the total of the amount of movement and the subtotal of the above amounts of blur is 8. In all of the first images a2, a3, and a4 and the second images b0, b1, and b2, the total of the amount of movement and the subtotal of the amount of blur is calculated in the above manner, and the total is shown in the predetermined column in the table 71. Out of these nine values, the first image a2 and the second image b2, which corresponds to the smallest case, are stored. In the case of the table 71, the first image a2 and the second image b2 having a total of 6 are stored.

The rate of match is a storage determination value, and may be calculated on the basis of the amount of blur and the amount of movement, or may be quantified and calculated using another selection condition such as a difference in brightness or a difference in time.

The display control unit 57 may perform control to display the first image and/or the second image stored by the storage unit 63 on the display in the target period ta. In the target period ta, the first illumination light beam is switched to the second illumination light beam and the second illumination light beam is emitted, and the image pickup sensor 45 acquires image signals for each frame. However, the stored first image and/or the stored second image may be continuously displayed on the display 18, in at least the target period ta.

Figure 25:
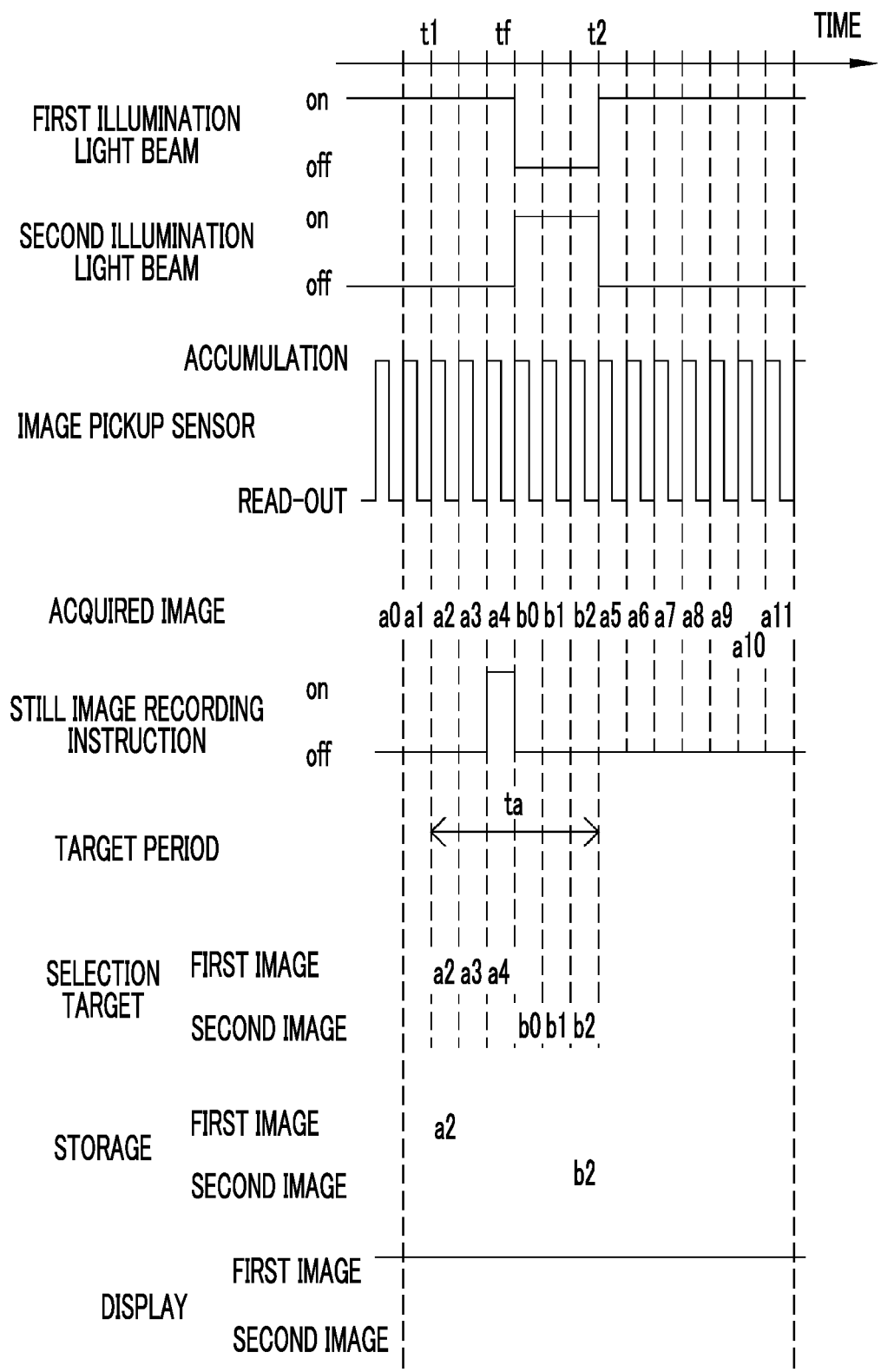
FIG. 25 is a diagram illustrating an example of selection of an image to be displayed on a display.

As shown in FIG. 25, in the first special observation mode, the light source processor 21 switches the first illumination light beam to the second illumination light beam at time tf of the still image recording instruction, and switches the second illumination light beam to the first illumination light beam which is emitted before the still image recording instruction to emit the first illumination light beam when time t2 which is the end point of the target period ta is passed. The display control unit 57 displays the first image on the display 18 in the first special observation mode. Then, the illumination light beam is switched from the first illumination light beam to the second illumination light beam at time tf of the still image recording instruction, but the first image is continuously displayed in the target period ta.

It is assumed that the first image displayed in the target period ta is the first image a2 stored by the still image recording instruction. As the first image displayed in the target period ta, the first image a4 which is a first image acquired immediately before the illumination light beam is switched from the first illumination light beam to the second illumination light beam at time tf of the still image recording instruction may be extended and displayed, and another first image may be displayed. Alternatively, the stored first image a2 and the stored second image b2 may be, for example, juxtaposed and displayed.

Figure 26:
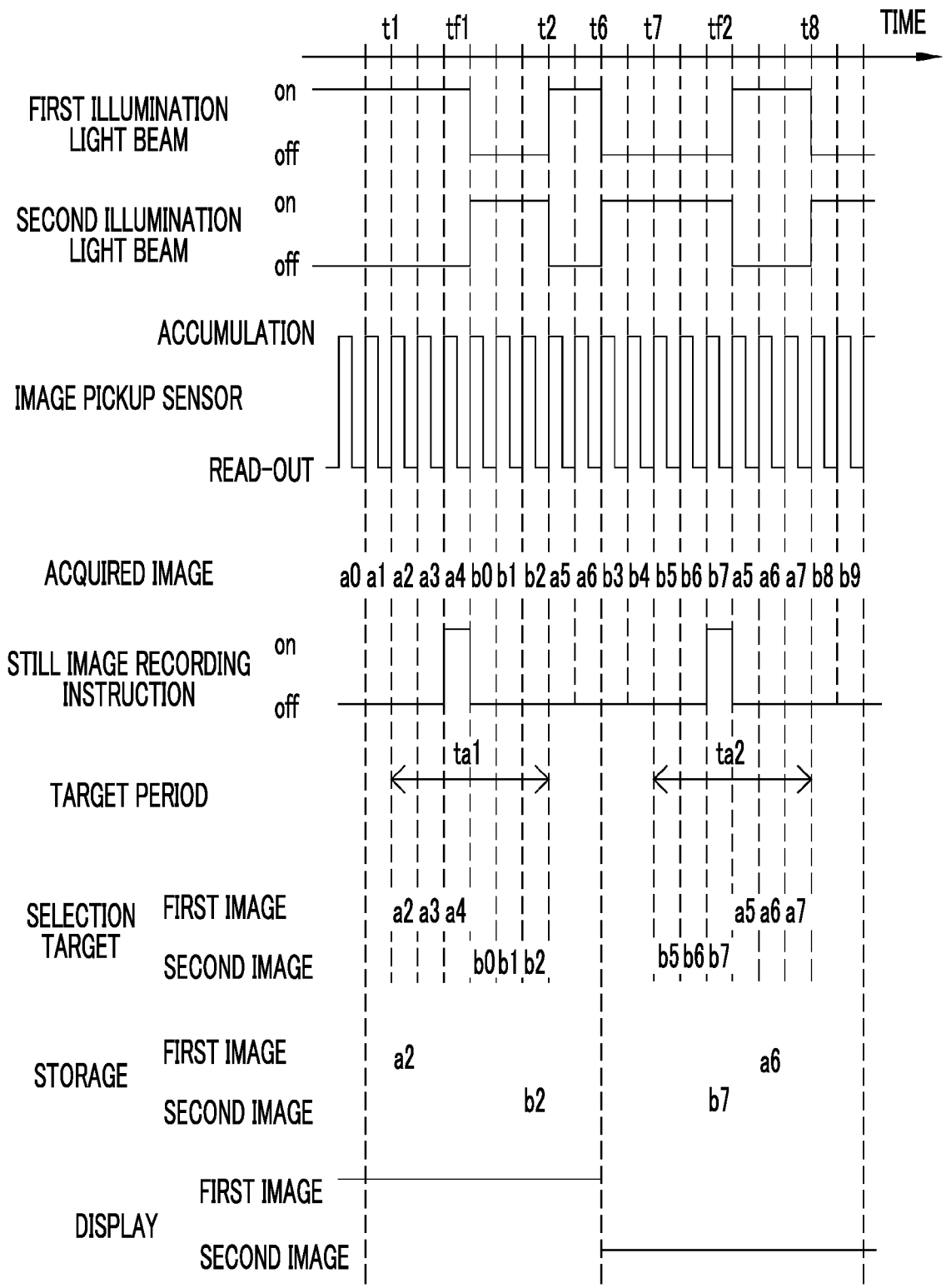
FIG. 26 is a diagram illustrating another example of the selection of an image to be displayed on the display.

As shown in FIG. 26, in the multi-observation mode, the light source processor 21 switches the first illumination light beam to the second illumination light beam at time tf1 of the still image recording instruction, and switches the second illumination light beam to the first illumination light beam which is emitted before the still image recording instruction to emit the first illumination light beam when time t2 which is the end point of a target period ta1 is passed. Then, the first illumination light beam is switched to the second illumination light beam at time t6 by the periodic switching between illumination light beams performed by the light source processor 21. The light source processor 21 switches the second illumination light beam to the first illumination light beam at time tf2 of the still image recording instruction, and switches the first illumination light beam to the second illumination light beam which is emitted before the still image recording instruction to emit the second illumination light beam when time t8 which is the end point of a target period ta2 is passed.

The display control unit 57 displays the first image on the display 18 during the period in which the illumination light beam is the first illumination light beam, in the multi-observation mode. Then, the illumination light beam is switched from the first illumination light beam to the second illumination light beam at time tf1 of the still image recording instruction, but the first image is continuously displayed in the target period ta1. It is assumed that the first image displayed in the target period ta1 is the first image a2 stored by the still image recording instruction. After that, the second image is displayed on the display 18 in the period in which the illumination light beam is the second illumination light beam. Then, the illumination light beam is switched from the second illumination light beam to the first illumination light beam at time tf2 of the still image recording instruction, but the second image is continuously displayed in the target period ta2.

It is assumed that the second image displayed in the target period ta2 is a second image b7 stored by the still image recording instruction. As the first image displayed in the target period ta1, the first image a4 which is a first image acquired immediately before the illumination light beam is switched from the first illumination light beam to the second illumination light beam at time tf1 of the still image recording instruction may be extended and displayed, and another first image may be displayed. Alternatively, the stored first image a2 and the stored second image b2 may be, for example, juxtaposed and displayed. As the second image displayed in the target period ta2, the second image b7 which is a second image acquired immediately before the illumination light beam is switched from the second illumination light beam to the first illumination light beam at time tf2 of the still image recording instruction may be extended and displayed, and another second image may be displayed. Alternatively, the stored second image b7 and the stored first image a6 may be, for example, juxtaposed and displayed.

As described above, the display control unit 57 performs control to continuously display the first image on the display 18 during the first period in which the illumination light beam is the first illumination light beam, and continuously displays the second image on the display 18 during the second period in which the illumination light beam is the second illumination light beam, so that it is possible to display selected endoscopic images in a state suitable for comparison on the display 18 without the flicker or the like, while acquiring image signals of a mode different from the mode the user is observing. Accordingly, the user can perform observation and the like more stably.

In the plurality of first images and the plurality of second images acquired in the target period, there may be no image satisfying the condition depending on the selection condition. In this case, for example, it is preferable to provide an alert unit that gives an alert to notify the user. The alert unit gives an alert to notify the user that there is no image satisfying the selection condition. Details on alerts, such as whether or not to give an alert in a case where there is not even one image satisfying the selection condition, how to give an alert, or whether to store images even in a case where the images do not satisfy the selection condition are preset.

Further, in this case, it is preferable to provide a retry unit that performs a retry. The retry unit performs the image storage processing again in a case where there is no image satisfying the selection condition. Details, such as whether or not to perform a retry in a case where there is not even one image satisfying the selection condition, the number of times of retries, the setting of the time to perform a retry, and whether to prompt the user to perform the processing start operation, are preset.

With the above configuration, a case where the alert unit is provided is preferable because a flexible selection condition can be set and the user can immediately know that there is no image satisfying the selection condition even in a case where there is no image satisfying the selection condition. Further, a case where the retry unit is provided is preferable because the user can easily acquire images in a state suitable for storage.

Figure 27:
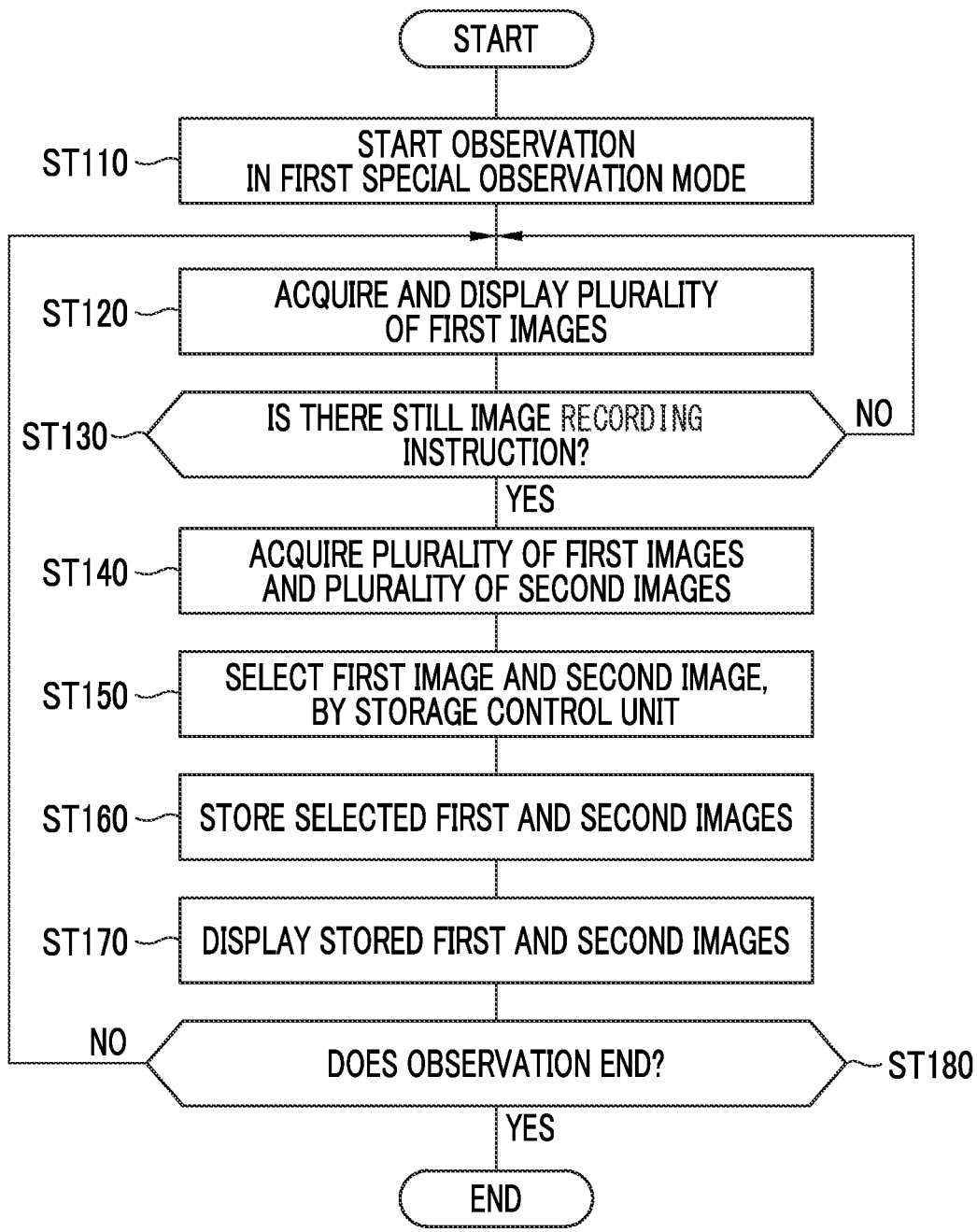
FIG. 27 is a flowchart showing a series of flows of storage of the still image in the first special observation mode.

Next, a series of flows of still image storage will be described with reference to the flowchart shown in FIG. 27. In the case of the first special observation mode, observation is performed in the first special observation mode (step ST110). During the observation, the image signal acquisition unit 51 acquires the first image (step ST120). In this case, as the endoscopic image to be displayed on the display 18, the first image may be continuously displayed, or the first image and the already stored second image may be, for example, juxtaposed and displayed.

When there is a still image recording instruction (YES in step ST130), since the still image recording instruction is the processing start operation of the image storage processing, the illumination light beam is switched from the first illumination light beam to the second illumination light beam in the target period including the time of the still image recording instruction, and the image signal acquisition unit 51 acquires the plurality of first images and the plurality of second images (step ST140). The plurality of acquired first images and the plurality of acquired second images are stored in the temporary storage unit 62, and the storage control unit 61 selects one first image and one second image that satisfy the preset selection condition, from the temporary storage unit 62 (step ST150). In a case where there is no still image recording instruction (NO in step ST130), observation and the acquisition of the first image are continued. The selected first and second images are stored by the storage unit 63 (step ST160). The display control unit 57 displays the stored first and second images on the display 18 (step ST170). The display format is a preset format, and for example, two images are juxtaposed and displayed on the display 18. When the observation is completed (YES in step ST180), the series of flows ends. In a case where the observation is continued (NO in step ST180), the process returns to the observation in the first special observation mode.

In the above embodiment, the present invention is applied to the endoscope system that performs processing on the endoscopic image, but the present invention can also be applied to a medical image processing system that processes medical images other than the endoscopic image, in a case where the still image is stored.

In the above embodiment, the hardware structures of the light source processor, the image processor, and the processing units that execute various types of processing, such as the central control unit 59, the image signal acquisition unit 51, the DSP 52, the noise reduction unit 53, the memory 54, the signal processing unit 55, the image storage unit 56, the storage control unit 61, the temporary storage unit 62, the storage unit 63, the display control unit 57, and the video signal generation unit 58, which are provided in the processor device 16, are various processors to be described below. The various processors include, for example, a central processing unit (CPU) which is a general-purpose processor that executes software (programs) to function as various processing units, a programmable logic device (PLD) which is a processor having a changeable circuit configuration after manufacture, such as a field programmable gate array (FPGA), and a dedicated electrical circuit which is a processor having a dedicated circuit configuration designed to execute various processing.

One processing unit may be composed of one of these various processors or a combination of two or more of the processors of the same type or different types (for example, a plurality of FPGAs, or a combination of a CPU and an FPGA). Alternatively, a plurality of processing units may be composed of one processor. A first example in which a plurality of processing units is composed of one processor is an aspect in which one or more CPUs and software are combined to constitute one processor and the processor functions as a plurality of processing units, as typified by a computer such as a client or a server. A second example is an aspect in which a processor that realizes all of the functions of a system including a plurality of processing units with one integrated circuit (IC) chip is used, as typified by a system on chip (SoC) or the like. As described above, various processing units may be formed of one or more of the above various processors as hardware structures.

More specifically, the hardware structure of these various processors is an electrical circuit (circuitry) in which circuit elements, such as semiconductor elements, are combined.

EXPLANATION OF REFERENCES

10: endoscope system
12: endoscope
12a: insertion part
12b: operation part
12c: bendable portion
12d: distal end portion
12e: angle knob
12f: still image recording instruction portion
12g: mode changeover switch
12h: zoom operation portion
14: light source device
16: processor device
18: display
19: keyboard
20: light source unit
20a: V-LED
20b: B-LED
20c: G-LED
20d: R-LED
21: light source processor
22: light emission period setting unit
30a: illumination optical system
30b: image pickup optical system
41: light guide
42: illumination lens
43: objective lens
44: zoom lens
45: image pickup sensor
46: CDS/AGC circuit
47: A/D converter
51: image signal acquisition unit
52: DSP
53: noise reduction unit
54: memory
55: signal processing unit
56: image storage unit
57: display control unit
58: video signal generation unit
59: central control unit
61: storage control unit
62: temporary storage unit
63: storage unit
71: table
81a, 81b: slide bar
82a, 82b: slider
BM: background mucous membrane
BP: blue light image
VS1: superficial blood vessel
VS2: deep blood vessel
VP: violet light image
GRP: green and red light image
t1 to t5: time
tf, tf1, tf2: time when a still image recording instruction is given
ta, ta1, ta2: target period
tb: post-switching period
tc: post-processing start operation period
a0 to a11: first image
b0 to b9: second image
ST110 to ST180: step

What is claimed is:

1. An endoscope system comprising:
a plurality of semiconductor light sources that emits light beams having wavelength bands different from each other;
a light source processor that is configured to emit each of a plurality of illumination light beams of which combinations of light intensities among the plurality of semiconductor light sources are different from each other; and
an image processor,
wherein the image processor is configured to:
acquire a first image and a second image obtained by imaging an observation target illuminated with a first illumination light beam and a second illumination light beam included in the plurality of illumination light beams, respectively, for each frame, each frame corresponding to a period including at least an exposure period and a readout period of an image sensor;
continuously irradiate the first illumination light across a plurality of the frames and continuously acquire a plurality of the first images across the plurality of the frames;
continuously irradiate the second illumination light across a plurality of the frames and continuously acquire a plurality of the second images across the plurality of the frames;
perform image storage processing of storing a first image selected from a plurality of the continuously acquired first images and a second image selected from a plurality of the continuously acquired second images; and
select, when a processing start operation for starting the image storage processing is performed, a first image and a second image that satisfy a preset selection condition from the plurality of continuously acquired first images and the plurality of continuously acquired second images acquired in a target period including a time when the processing start operation is performed, for the image storage processing, and
the light source processor is configured to switch once and not more than once, out of the first illumination light beam and the second illumination light beam, from one being emitted to the other to be emitted in the target period.

2. The endoscope system according to claim 1, wherein the target period is a period in which the image processor acquires a plurality of the first images which is a preset number and a plurality of the second images which is a preset number.

3. The endoscope system according to claim 1, wherein the target period is a period in which the image processor acquires the first image and the second image that satisfy the selection condition.

4. The endoscope system according to claim 1, wherein the light source processor is configured to alternately switch and emit the first illumination light beam and the second illumination light beam at a preset cycle.

5. The endoscope system according to claim 1, wherein the light source processor is configured, in a case where the processing start operation is performed after a preset post-switching period has elapsed from a previous switch time between the first illumination light beam and the second illumination light beam, to switch from one which is emitted before the processing start operation to the other to be emitted, wherein the post-switching period is a preset period defined by a predetermined number of frames.

6. The endoscope system according to claim 5,
wherein the light source processor is configured to switch, out of the first illumination light beam and the second illumination light beam, from one which is emitted after the processing start operation to the other to be emitted, when the target period is passed.

7. The endoscope system according to claim 5,
wherein the light source processor is configured to switch, out of the first illumination light beam and the second illumination light beam, from one which is emitted after the processing start operation to the other to be emitted, when a preset period starting from the time of the processing start operation is passed.

8. The endoscope system according to claim 1,
wherein the light source processor is configured, in a case where the processing start operation is performed in a preset post-switching period starting from a previous switch time between the first illumination light beam and the second illumination light beam, to continuously emit one which is emitted before the processing start operation wherein the post-switching period is a preset period defined by a predetermined number of frames.

9. The endoscope system according to claim 8,
wherein the light source processor is configured to switch, out of the first illumination light beam and the second illumination light beam, from one which is emitted at the time of the processing start operation to the other to be emitted, when the preset period starting from the time when the light emission is switched between the first illumination light beam and the second illumination light beam is passed.

10. The endoscope system according to claim 8,
wherein the light source processor is configured to switch, out of the first illumination light beam and the second illumination light beam, from one which is emitted at the time of the processing start operation to the other to be emitted, when a preset period starting from the time of the processing start operation is passed.

11. The endoscope system according to claim 1,
wherein the image processor is configured to set the selection condition that a first image having least blur out of the plurality of acquired first images or a second image having least blur out of the plurality of acquired second images is selected.

12. The endoscope system according to claim 1,
wherein the image processor is configured to set the selection condition that a first image and a second image having smallest positional deviation between the first image selected from the plurality of acquired first images and the second image selected from the plurality of acquired second images are selected.

13. The endoscope system according to claim 1,
wherein the image processor is configured to set the selection condition that a first image and a second image having a smallest difference in brightness between the first image selected from the plurality of acquired first images and the second image selected from the plurality of acquired second images are selected.

14. The endoscope system according to claim 1,
wherein the image processor is configured to set the selection condition that a first image and a second image having a smallest difference in acquisition time between the first image selected from the plurality of acquired first images and the second image selected from the plurality of acquired second images are selected.

15. The endoscope system according to claim 1, further comprising:
a display that displays the first image and/or the second image,
wherein the image processor is configured to display the stored first image and/or the stored second image on the display in the target period.

16. A method of operating an endoscope system including a plurality of semiconductor light sources that emits light beams having wavelength bands different from each other,
a light source processor that is configured to emit each of a plurality of illumination light beams of which combinations of light intensities among the plurality of semiconductor light sources are different from each other, and
an image processor, the method comprising:
acquiring, by the image processor, a first image and a second image obtained by imaging an observation target illuminated with a first illumination light beam and a second illumination light beam included in the plurality of illumination light beams, respectively, for each frame, each frame corresponding to a period including at least an exposure period and a readout period of an image sensor;
continuously irradiating, by the image processor, the first illumination light across a plurality of the frames and continuously acquiring a plurality of the first images across the plurality of the frames;
continuously irradiating, by the image processor, the second illumination light across a plurality of the frames and continuously acquiring a plurality of the second images across the plurality of the frames;
performing, by the image processor, image storage processing of storing a first image selected from a plurality of the continuously acquired first images and a second image selected from a plurality of the continuously acquired second images;
selecting, by the image processor, when a processing start operation for starting the image storage processing is performed, a first image and a second image that satisfy a preset selection condition from the plurality of continuously acquired first images and the plurality of continuously acquired second images acquired in a target period including a time when the processing start operation is performed, for the image storage processing; and
switching once and not more than once, by the light source processor, out of the first illumination light beam and the second illumination light beam, from one being emitted to the other to be emitted in the target period.

* * * * *